(12) United States Patent
Kato

(10) Patent No.: US 8,789,949 B2
(45) Date of Patent: Jul. 29, 2014

(54) CORNEA IMAGING APPARATUS AND CORNEA IMAGING METHOD

(71) Applicant: Tomey Corporation, Nagoya (JP)

(72) Inventor: Chihiro Kato, Nagoya (JP)

(73) Assignee: Tomey Corporation, Nagoya-shi (JP)

( * ) Notice: Subject to any disclaimer, the term of this patent is extended or adjusted under 35 U.S.C. 154(b) by 0 days.

(21) Appl. No.: 13/857,631

(22) Filed: Apr. 5, 2013

(65) Prior Publication Data

US 2013/0278898 A1      Oct. 24, 2013

(30) Foreign Application Priority Data

Apr. 19, 2012   (JP) ................................. 2012-095408

(51) Int. Cl.
*A61B 3/14*        (2006.01)
(52) U.S. Cl.
CPC ................ *A64B 3/1005* (2013.01); *A61B 3/14* (2013.01)
USPC ........................... 351/208; 351/206; 351/210
(58) Field of Classification Search
CPC ........ A61B 3/14; A61B 3/107; A61B 3/1005; A61B 19/5212; A61F 2009/00872
USPC .............. 351/205, 206, 208, 210, 246; 606/4
See application file for complete search history.

(56) References Cited

U.S. PATENT DOCUMENTS

| 5,557,351 | A | 9/1996 | Kasahara et al. |
| 6,164,778 | A | 12/2000 | Takagi et al. |
| 7,572,010 | B2 | 8/2009 | Nishio et al. |

FOREIGN PATENT DOCUMENTS

| DE | 10138158 A1 | 2/2003 |
| EP | 1 974 657 A2 | 10/2008 |
| JP | B2-2580464 | 2/1997 |
| JP | B2-3338529 | 10/2002 |
| JP | A-2007-215956 | 8/2007 |

OTHER PUBLICATIONS

Jul. 26, 2013 Extended European Search Report issued in European Patent Application No. 13164149.0.

*Primary Examiner* — Mahidere Sahle
(74) *Attorney, Agent, or Firm* — Oliff PLC

(57) ABSTRACT

A cornea imaging apparatus including: a collimation axis holding mechanism; an imaging mechanism; a Z-direction actuating means; an X-direction actuating means and a Y-direction actuating means; an inclination angle changing means that changes an inclination angle of an imaging center axis of the imaging mechanism against a collimation axis of an eye under examination; an endothelial configuration computing means that determines a corneal endothelial configuration; and a normal vector computing means that determines a normal vector direction at a given imaging position of the corneal endothelial configuration, wherein at the imaging position, the inclination angle and positions in the Z and X directions are set adjusted so as to align the imaging center axis of the imaging mechanism with the normal vector direction determined by the normal vector computing means.

10 Claims, 17 Drawing Sheets

CORNEA IMAGING APPARATUS AND CORNEA IMAGING METHOD

INCORPORATED BY REFERENCE

The disclosure of Japanese Patent Application No. 2012-095408 filed on Apr. 19, 2012 including the specification, drawings and abstract is incorporated herein by reference in its entirety.

BACKGROUND OF THE INVENTION

1. Field of the Invention

The present invention relates to a cornea imaging apparatus for imaging corneal endothelial cells by means of directing illumination light into an eye under examination and receiving light reflected from the cornea thereof, and a cornea imaging method.

2. Description of the Related Art

Conventionally, observation of the cornea of the eye, and in particular of the cellular status of the corneal endothelium, has been commonly carried out in determining a presence of ocular disorders or making a diagnosis of postoperative prognosis.

In order to observe such cellular status of the corneal endothelium, there has been known a cornea imaging apparatus capable of imaging corneal endothelial cells without contacting the eye under examination. This cornea imaging apparatus is designed to direct a slit beam of illumination light (slit light flux) from an illumination optical system into the cornea of the eye under examination at an angle and receive the light reflected from the cornea by an imaging optical system to take images of the corneal endothelial cells.

Meanwhile, in taking images of the corneal endothelium, there are sometimes needs for covering a wide area including not only the center portion of the cornea but also the peripheral portion thereof. To meet such requirements, Japanese Patent No. 2580464 has proposed a structure, wherein images of the corneal periphery are taken by irradiating a slit light flux for taking images on the corneal periphery by letting the test subject fixate in an oblique direction away from straight ahead and imaging the reflected light flux with an imaging optical system.

However, in the cornea imaging apparatus described in Japanese Patent No. 2580464, clear images of corneal endothelium could not be obtained in some cases since imaging of the corneal endothelium in the corneal periphery is performed through an XY alignment of the imaging optical system using specularly reflected light from the corneal epithelium (also called ectocornea) in the same way as for the center portion of the cornea. As anatomically evident, this is caused by the difference in curvature of the corneal endothelium from that of the corneal epithelium, and in the peripheral portion, performing the XY alignment using the specularly reflected light from the corneal epithelium in the same direction can move the alignment away from the optimum position of the corneal endothelium, although the XY alignment of the corneal endothelium can be performed using the specularly reflected light from the corneal epithelium at the corneal center.

In other words, under a state where the test subject fixates straight ahead to get images of the corneal center taken, the optical axis (marked with ●) of the XY alignment light reflected from the corneal epithelium is aligned with the optical axis (marked with x) of the light reflected from the corneal endothelium, as shown in FIG. 18A, so that the corneal endothelium and corneal epithelium share the same optical axis by the performance of an XY alignment within the imaging area marked with □, thus enabling more accurate imaging of the targeted endothelium. However, under a state where the test subject fixates in an oblique direction to get images of the corneal periphery taken, the optical axis (marked with x) of the light reflected from the endothelium can be moved from the optical axis (marked with ●) of the XY alignment light reflected from the corneal epithelium so that the accuracy of endothelium imaging is significantly degraded even with the XY alignment due to the difference of optical axes between the corneal endothelium and corneal epithelium.

In summary, in order to take clear images of the corneal endothelium, it is necessary to do it after moving the setting of the imaging area (marked with □) by a given distance from the center point (marked with ●) of the XY alignment in the shift direction of the corneal endothelium (marked with x) in FIG. 18B.

For that reason, in case of taking wide-range cornea images in a conventional way with a cornea imaging apparatus and failing to obtain clear images, the imaging process was repeated until satisfactory images are obtained by having the tester move the relative position of the imaging optical system against the eye under examination in the XY direction for positioning. That imposed a significant burden on the tester and the test subject and much time was required for an inexperienced tester to complete the imaging, which is likely to inflict pain on the test subject.

To deal with these problems, U.S. Pat. No. 5,557,351 and Japanese Patent No. 3338529 propose a cornea imaging apparatus that presets the amount of correction of the XY alignment against the eye under examination corresponding to the position in the oblique direction that the eye under examination fixates so as to adjust the XY alignment position determined by the XY alignment signal obtained from the light reflected from the corneal epithelium by the amount of correction corresponding to the selected fixation target. Here, it is conceived that the preset amount of correction of the XY alignment can be specified from anatomical data based on, for example, the theory of difference in curvature between the corneal endothelium and corneal epithelium in the shift direction α in FIG. 18B.

However, investigations performed by the inventor revealed that there were many cases where wide range cornea images cannot be taken with enough accuracy even if the XY alignment following the technology described in U.S. Pat. No. 5,557,351 and Japanese Patent No. 3338529 of the prior art is adopted. Upon examination of any possible cause by the inventor, it was revealed that individual differences exist in the curvature radius of the corneal endothelium and corneal epithelium, and the extent of these differences is sometimes significant enough to affect the imaging accuracy. What is especially noteworthy is the fact that many of those who need imaging of their corneal endothelium are patients who have ocular disorders or require postoperative follow-up, not the general public, and that the curvatures of the corneal endothelium and conical epithelium often differ much in those patients.

Considering these facts, in the cornea imaging apparatus described in the above U.S. Pat. No. 5,557,351 and Japanese Patent No. 3338529 that adopt the preset amount of correction based on the assumption that the individual differences in the curvature radius of the corneal endothelium are surely small enough not to affect the imaging accuracy in light of the anatomical statistical data, it occurs relatively often that the amount of correction is inappropriate, and after all, the tester needs to fine-tune the imaging position in actual on-site uses, and in that sense, the cornea imaging apparatus described in U.S. Pat. No. 5,557,351 and Japanese Patent No. 3338529 as the prior art should be considered nothing more than an imaging apparatus equipped with a semi-automatic alignment mechanism.

SUMMARY OF THE INVENTION

Here, the present invention was made against the background described above, and the problem to be solved thereby is to enable speedier imaging with further reduced burden imposed on the tester and the test subject in taking images of the corneal endothelium, and to provide a novel cornea imaging apparatus and a novel method of imaging the cornea, with high accuracy, capable of imaging corneal endothelial cells in a wide range including not only the central portion but also the peripheral portion, even with individual differences in the curvature radius of the corneal endothelium and epithelium.

Modes of the present invention designed to solve the above problems will be described below. The constituting elements adopted in each of the modes described below can be adopted in any combination as possible.

A first mode of the present invention related to a cornea imaging apparatus provides a cornea imaging apparatus including; (A) a collimation axis holding mechanism including a fixation target that keeps a collimation axis of an eye under examination at a given position; (B) an imaging mechanism containing an illumination optical system with an illumination light source that obliquely illuminates a slit light flux on the eye under examination and a cornea imaging optical system having a photoelectric element that takes images of a corneal endothelium by receiving the slit light flux reflected from a cornea of the eye under examination; (C) a Z-direction actuating means that moves the imaging mechanism in a Z direction which is a direction of getting closer to or away from the eye under examination; (D) an X-direction actuating means and a Y-direction actuating means that move the imaging mechanism in X and Y directions respectively that are perpendicular to the Z direction; (E) an inclination angle changing means that changes an inclination angle of an imaging center axis of the imaging mechanism against the collimation axis of the eye under examination under a state where a position of the collimation axis of the eye under examination fixed and retained by the fixation target; (F) an endothelial configuration computing means that determines a corneal endothelial configuration of the eye under examination; and (G) a normal vector computing means for the endothelium that determines a normal vector direction at a given imaging position of the corneal endothelial configuration determined by the endothelial configuration computing means, wherein at the imaging position, the inclination angle set by the inclination angle changing means and positions in the Z and X directions set by the Z and X direction actuating means, respectively, are set adjusted so as to align the imaging center axis of the imaging mechanism with the normal vector direction determined by the normal vector computing means for the endothelium.

According to the cornea imaging apparatus structured as in the present invention, (F) the corneal endothelial configuration of the eye under examination is determined by the endothelial configuration computing means, and (G) the normal vector direction of the corneal endothelium is determined by the normal vector computing means for the endothelium. Then, the imaging center axis of the imaging mechanism (i.e. a bisector of the angle created by optical axes of the illumination optical system and endothelium imaging optical system) is aligned with the obtained normal vector direction of the corneal endothelium by (E) the inclination angle changing means, (C) the Z-direction actuating means, and (D) the X-direction actuating means so as to take images of the corneal endothelium. Thus, according to the present invention, images of the corneal endothelial cells can be taken with higher accuracy by aligning the imaging center axis not with the corneal epithelium but directly with the normal vector direction of the corneal endothelium, which is the imaging target. Particularly, in the area where the curvature of the corneal endothelium is much shifted from the curvature of the corneal epithelium, like in the corneal periphery, aligning the imaging center axis of the imaging mechanism with the normal vector direction of the corneal endothelium, according to the present invention, makes it possible to take clear images of the endothelium in the corneal periphery, too. In addition, the imaging center axis of the imaging mechanism can be aligned surely and quickly with the normal vector direction of the corneal endothelium by means of mechanical movements of (E) the inclination angle changing means, (C) the Z-direction actuating means, and (D) the X-direction actuating means, thus allowing to reduce the time for imaging and the burden imposed on the test subject.

Also, by individually adjusting the imaging center axis of the imaging mechanism for the inclination angle by (E) the inclination angle changing means, the position in the Z direction by (C) the Z-direction actuating means, and the position in the X direction by (D) the X-direction actuating means, it is possible to align said axis with the normal vector direction at any position of the corneal endothelium. Therefore, even if the variations of curvature radii of the corneal endothelium and corneal epithelium are much larger than those in the anatomical data, it is possible to take clear images of said portions by properly aligning the imaging center axis of the imaging mechanism with the normal vector direction at a given position of the corneal endothelium while minimizing the change of the location of the imaging mechanism. As a result, images can be taken over a wide area with high accuracy.

(E) The inclination angle changing means that changes the inclination angle of the imaging center axis of the imaging mechanism relative to the collimation axis of the eye under examination can be anything as long as it changes the inclination angle of the imaging center axis relative to the collimation axis and, for example, it can be carried out by a mechanism that displaces the imaging mechanism in oscillation in the circumferential direction of the eye under examination, or by a mechanism that makes the imaging center axis of the imaging mechanism rotatable around a given vertical axis and so forth.

Also, (C) the Z-direction actuating means that moves (B) the imaging mechanism in the Z direction and (D) the X-direction actuating means that moves the imaging mechanism in the X direction can be either the one that moves the same together with another mechanism such as (A) the collimation axis holding mechanism including the above fixation target, or the one that moves only the imaging mechanism in the Z or X direction independently from (A) the collimation axis holding mechanism and the like.

A second mode of the present invention related to the cornea imaging apparatus provides the one according to the above first mode, wherein the inclination angle changing means comprises an oscillation mechanism that displaces the imaging mechanism in oscillation in the circumferential direction of the eye under examination.

According to the present mode, the imaging center axis of the imaging mechanism can be displaced at an inclination by the oscillation mechanism in a form of a circular arc relatively similar to the curvature of the corneal endothelium. This enables more accurate adjustments of the inclination angle than when the imaging mechanism is rotated around a given vertical axis.

More preferably, the oscillation center of the oscillation mechanism is set at the curvature center of the corneal endothelium of the eye under examination or in the proximity thereof. This allows the imaging center axis of the imaging mechanism to be more favorably aligned with the normal vector direction of the corneal endothelium at a given position while minimizing the change of the location of the imaging mechanism.

A third mode of the present invention related to the cornea imaging apparatus provides the one according to the above first or second mode, wherein the imaging position is set at multiple locations in the circumferential direction of the eye under examination, and at the multiple locations, the imaging center axis of the imaging mechanism is set adjusted in sequence to the normal vector direction determined by the normal vector computing means for the endothelium under the state where the position of the collimation axis is fixed and retained by the fixation target so as to take consecutive images.

According to the present mode, at the imaging positions set at multiple locations in the circumferential direction of the eye under examination, the corneal endothelial cells can be imaged consecutively by aligning the imaging center axis with the normal vector direction of the corneal endothelium in sequence, thus enabling to take wide-range images of the corneal endothelium. And according to the present invention, moving the imaging mechanism in the circumferential direction of the eye under examination by (E) the inclination angle changing means, (C) the Z-direction actuating means, and (D) the X-direction actuating means allows to take consecutive images at multiple locations keeping the collimation axis of the eye under examination fixed, and at the same time, to take clear images of the corneal endothelium in a wide range by aligning the imaging center axis to the normal vector direction of the corneal endothelium.

A fourth mode of the present invention related to the cornea imaging apparatus provides the one according to any one of the above first to third modes, wherein the corneal endothelial configuration of the eye under examination is obtained by determining an estimated curvature value of the corneal endothelium using measured values of the cornea according to the endothelial configuration computing means.

More preferably, a fifth mode of the present invention related to the cornea imaging apparatus provides the one according to the above fourth mode, wherein the estimated curvature value of the corneal endothelium is determined by measured values of a thickness of the cornea at not less than three locations apart from each other in the circumferential direction of the eye under examination according to the endothelial configuration computing means.

These measured values of the corneal thickness can be obtained based on the information on the light quantity distribution detected by a line sensor and the displacement distance of an optical system from the point of detecting the corneal epithelium to the point of detecting the corneal endothelium read by a photo diode. Also the estimated curvature value of the corneal endothelium can be calculated by solving a system of equations with three unknowns by a circle equation $(x-a)^2+(y-b)^2=R^2$. According to these modes, a curvature close enough to the actual endothelial configuration can be estimated since the curvature of the corneal endothelium is estimated based on measured values of the corneal thickness. In case of imaging a portion formed relatively close to a spherical curve such as near the center of the cornea, it is possible to take the image using the estimated curvature as the curvature of the corneal endothelium, which allows faster image taking. Particularly, according to the fifth mode, the curvature can be estimated more accurately and the normal vector direction at each imaging position can be determined more securely and quickly since the curvature is estimated based on measured values at not less than three locations.

A sixth mode of the present invention related to the cornea imaging apparatus provides the one according to the above fourth or fifth mode, wherein the estimated curvature value of the corneal endothelium is followed in the endothelial configuration computing means and measurements of endothelium positions are taken based on the flux reflected from the cornea at multiple measurement points on the corneal endothelium, and the corneal endothelial configuration is obtained based on the measurements taken at the multiple measurement points.

According to the present mode, the corneal endothelial configuration closer to the actual one can be obtained since the corneal endothelial configuration is obtained by measuring the endothelium position at multiple points following the estimated curvature of the corneal endothelium. This allows the normal vector direction of the endothelium at each imaging position to be more closely aligned with the actual endothelial configuration. In the present mode, it is preferable to measure the endothelium position at proper intervals and determine the endothelium position between the measurement points by the Lagrange interpolation, spline interpolation or hyperbolic functions in terms of processing speed, but it can also be done without using the interpolation methods and the like by measuring the endothelium position at multiple locations in the circumferential direction of the eye under examination.

A seventh mode of the present invention related to the cornea imaging apparatus provides the one according to any one of the above first to sixth modes, wherein the Z-direction actuating means and X-direction actuating means comprise an imaging direction actuating means that moves the imaging mechanism in a direction of the imaging center axis.

According to the present mode, the focal position (intersection between an optical axis of the illumination optical system and that of the corneal imaging optical system) can be moved along the imaging center axis. Therefore, in moving the focal position of the imaging mechanism onto the corneal endothelium where the imaging position is, the imaging mechanism can be moved to the imaging position by moving the focal position of the imaging mechanism with the imaging direction actuating means once the imaging center axis of the imaging mechanism is aligned with the normal vector direction of the corneal endothelium using the inclination angle changing means as well as Z-direction actuating means or X-direction actuating means. Thus, using the imaging direction actuating means complementary to the Z-direction actuating means and X-direction actuating means makes it possible to fine-tune the movements of the imaging mechanism in the Z and X directions at the same time, thus enabling to move the imaging mechanism easily and quickly.

An eighth mode of the present invention related to the cornea imaging apparatus provides the one according to any one of the above first to seventh modes, wherein a keratometer that measures a corneal front curvature of the eye under examination on a horizontal plane is configured to comprise the collimation axis holding mechanism and a kerato-ring light source that directs multiple spot lights into the eye under examination around an optical axis of the fixation target.

According to the present mode, the corneal front curvature of the eye under examination can be measured on a horizontal plane. This allows the position of the corneal endothelium to be estimated more accurately based on the measured corneal front curvature and measured corneal thickness. This can also be used for evaluation of astigmatism and the like since using the cornea imaging apparatus of the present invention enables actual measurements of the corneal front curvature.

The first mode of the present invention related to a cornea imaging method provides the method of imaging the cornea of the eye under examination, the method including: using the cornea imaging apparatus defined in any one of the first to eighth modes of the present invention related to the cornea imaging apparatus; an endothelial configuration computing step that determines the corneal endothelial configuration of the eye under examination by the endothelial configuration computing means under a state where the position of the collimation axis of the eye under examination is fixed and retained by the fixation target; a normal vector computing step of the endothelium that determines by the normal vector computing means for the endothelium the normal vector direction at a given imaging position of the corneal endothelial configuration; and a position adjusting step of the imaging mechanism that, at the imaging position, adjusts and sets the inclination angle by the inclination angle changing means and the position in the Z direction by the Z-direction actuating means and the position in the X direction by the X-direction actuating means so as to align the imaging center axis of the imaging mechanism with the normal vector direction determined by the normal vector computing means for the endothelium.

According to the cornea imaging method following the present invention, the normal vector direction of the corneal endothelium is determined in the endothelial configuration computing step and the normal vector computing step for the endothelium while the imaging center axis of the imaging mechanism is aligned with the obtained normal vector direction of the corneal endothelium. This allows the corneal endothelial cells to be imaged more accurately. Particularly, since the imaging center axis is aligned with the normal vector direction of the corneal endothelium, it is possible to take accurate images of the corneal endothelial cells even if the curvature of the corneal endothelium is significantly different from that of the corneal epithelium, thus enabling clear imaging of the endothelium surrounding the cornea.

The second mode of the present invention related to the cornea imaging method provides the one according to the above first mode, further including a consecutive imaging step wherein the imaging position is set at multiple locations in the circumferential direction of the eye under examination and the imaging center axis of the imaging mechanism is set adjusted in sequence to the normal vector direction determined by the normal vector computing means for the endothelium to take consecutive images at the multiple locations under a state where the position of the collimation axis of the eye under examination is fixed and retained by the fixation target.

In the consecutive imaging step according to the present mode, images of the corneal endothelium can be taken at multiple locations in the circumferential direction of the eye under examination. According to the present invention, in the position adjusting step of the imaging mechanism, images can be taken at multiple locations keeping the collimation axis of the eye under examination fixed by means of moving the imaging mechanism in the circumferential direction of the eye under examination.

According to the cornea imaging apparatus and the cornea imaging method following the present invention, the corneal endothelial cells can be imaged more clearly by means of aligning the imaging center axis of the imaging apparatus with the normal vector direction of the corneal endothelium. Also, changeable inclination angle of the imaging center axis of the imaging mechanism relative to the collimation axis makes it possible to take images at multiple locations keeping the collimation axis of the eye under examination fixed, thus enabling to take a wide range of clear images of the corneal endothelium while reducing the burden imposed on the tester and the test subject.

BRIEF DESCRIPTION OF THE DRAWINGS

The foregoing and/or other objects, features and advantages of the invention will become more apparent from the following description of a preferred embodiment with reference to the accompanying drawings in which like reference numerals designate like elements and wherein.

DETAILED DESCRIPTION OF PREFERRED EMBODIMENTS

Figure 1:
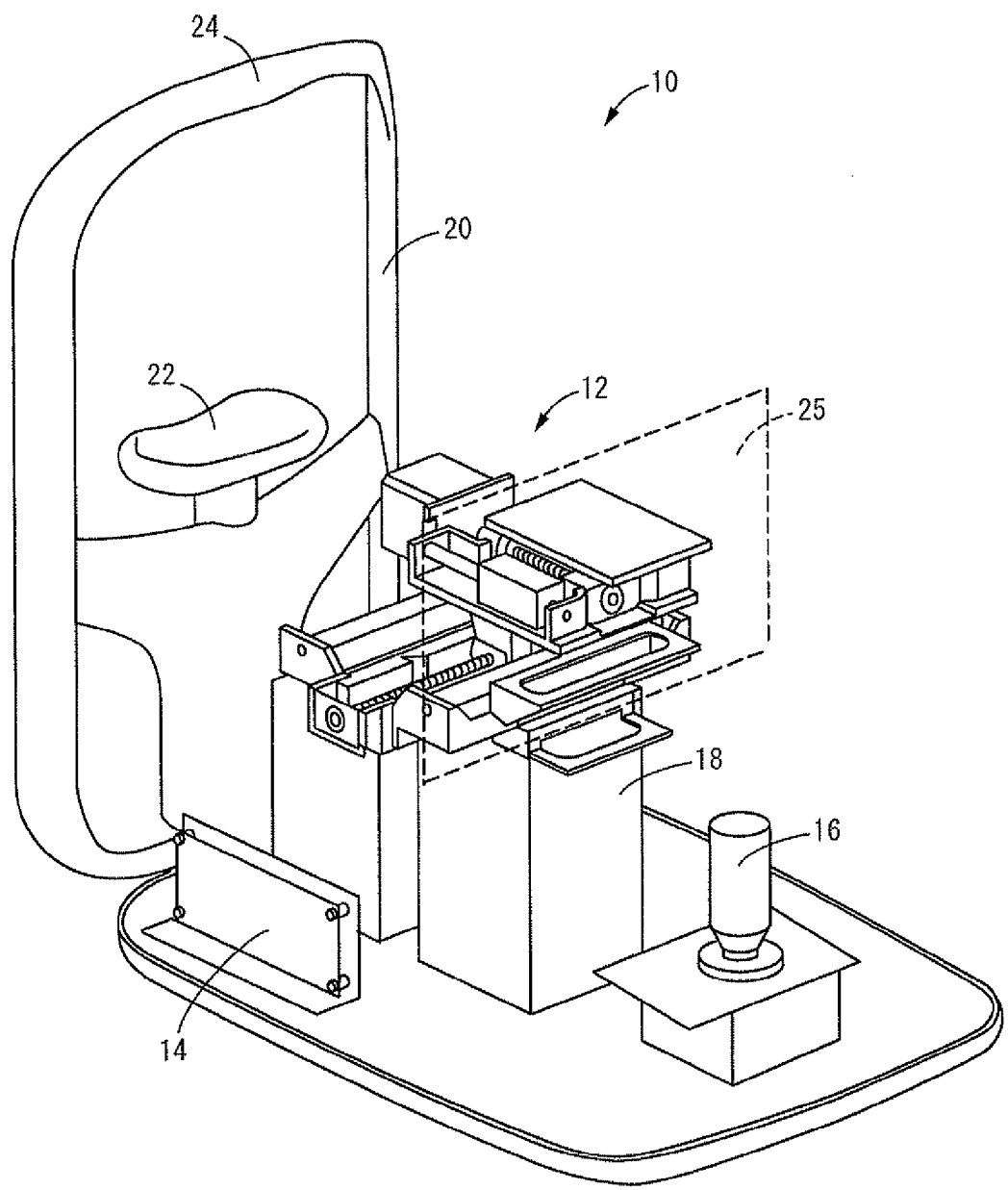
FIG. 1 is an illustrative drawing for explaining a cornea imaging apparatus as a first embodiment of the present invention.

First, FIG. 1 schematically shows a cornea imaging apparatus 10 with the housing removed as a first embodiment of the present invention. The cornea imaging apparatus 10 is provided with an instrumental optical system 12, a control unit 14, an operation stick 16 and so forth. The instrumental optical system 12, arranged on a base 18 is movable thereon in three axial directions perpendicular to each other based on operations of the operation stick 16 and control instructions from the control unit 14. The cornea imaging apparatus 10 is also provided with a support table 20. The support table 20 is provided with a chin support 22 and a forehead pad 24 that fix the test subject's face looking toward the instrumental optical system 12 by having the test subject's chin on the chin support 22 and the forehead placed against the forehead pad 24. In addition, as shown schematically, the cornea imaging apparatus 10 is provided with a display monitor 25 made of a liquid crystal material and the like, for example.

Figure 2:
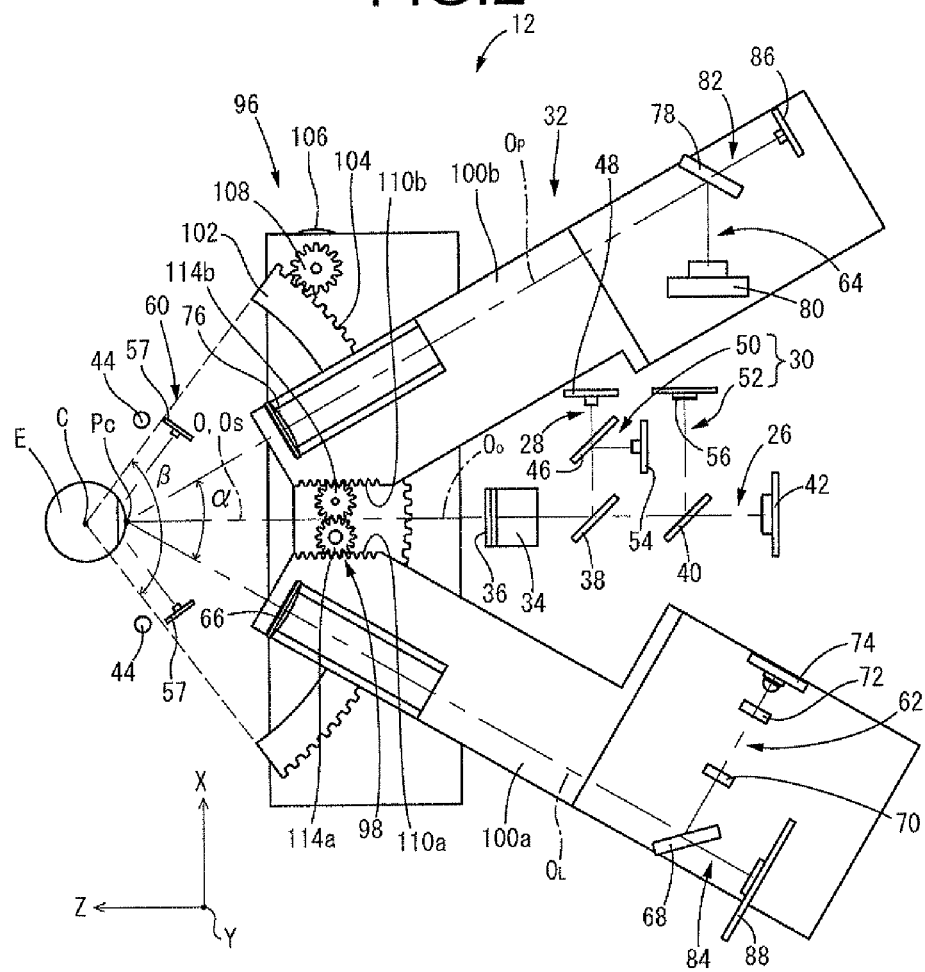
FIG. 2 is an illustrative drawing showing an upper view of an instrumental optical system of the first embodiment of the present invention.
Figure 3:
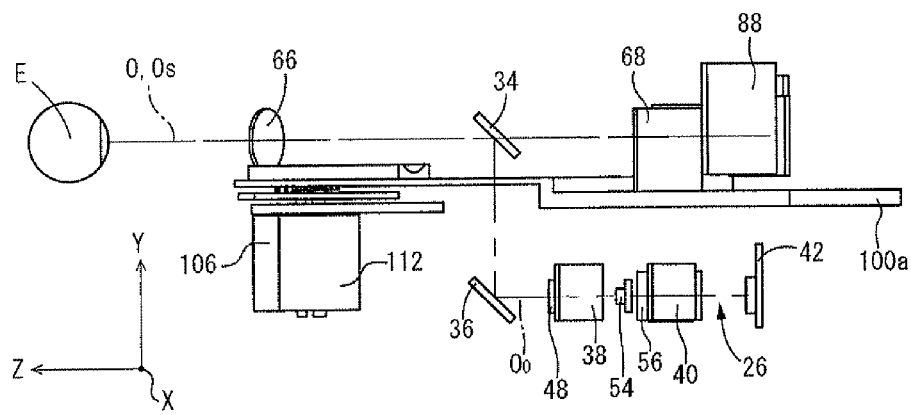
FIG. 3 is an illustrative drawing showing a side view of the instrumental optical system of the first embodiment of the present invention.

FIGS. 2 and 3 show the instrumental optical system 12. The instrumental optical system 12 is provided with an observation optical system 26 for observing the front portion of the eye under examination E, a fixation target optical system 28 as a collimation axis holding mechanism for fixing the collimation of the eye under examination E, an XY alignment optical system 30 for positioning the instrumental optical system 12 at the eye under examination E, and a specular optical system 32 as an imaging mechanism for imaging the corneal endothelium of the eye under examination E. In the illustrative drawing of FIG. 3, observation light sources 44, 44 and kerato-ring light sources 57, 57, all described later, are omitted.

The observation optical system 26 is configured to include, in the following order from the position nearest the eye under examination E, a mirror 34, a mirror 36, a half mirror 38, a half mirror 40, and an observation CCD 42. Also, in front of the eye under examination E, a plurality of (two in the present embodiment) observation light sources 44, 44 are arranged. For the observation light sources 44, 44, infrared LEDs, for example, that emit an infrared light flux is used. Then, the light fluxes emitted from the observation light sources 44, 44 and reflected from the front portion of the eye under examination E are reflected by the mirror 34 and mirror 36 to form an image on the observation CCD 42. Thus, the optical axis $O_O$ of the observation optical system 26 of the present embodiment is aligned with the front-sight axis O during the section between the eye under examination E and the mirror 34, while being set offset from the front-sight axis O of the eye under examination E during the section between the mirror 34 and the observation CCD 42 after the reflections at the mirror 34 and mirror 36.

The fixation target optical system 28 is configured to be provided with, in the following order from the position nearest the eye under examination E, the mirror 34, the mirror 36, the half mirror 38, a half mirror 46, and a fixation target light source 48, The fixation target light source 48 is a light source that emits visible light such as an LED, for example, and a light flux emitted from the fixation target light source 48 is reflected by the half mirror 38 and the mirrors 36 and 34 to be directed into the eye under examination E.

The XY alignment optical system 30 is configured to include an XY alignment illumination optical system 50 and an XY alignment detection optical system 52. The XY alignment illumination optical system 50 is configured to be provided with, in the following order from the position nearest the eye under examination E, the mirror 34, the mirror 36, the half mirror 38, the half mirror 46, and an XY alignment light source 54. The XY alignment light source 54 emits an infrared light beam as reference light for XY alignment, which passes through a pinhole plate, not shown, and is reflected by the half mirror 46 and turned to parallel light fluxes by a project lens, not shown, before being reflected by the half mirror 38 and mirrors 36 and 34 to be projected on the cornea of the eye under examination on the optical axis $O_O$ of the observation optical system 26 that becomes the front-sight of the eye under examination E.

Meanwhile, the XY alignment detection optical system 52 is configured to be provided with, in the following order from the position nearest the eye under examination E, the mirror 34, the mirror 36, the half mirror 40, and an XY alignment sensor (profile sensor) 56 that can detect positions. Then, the light flux projected from the XY alignment light source 54 on the eye under examination E and specularly reflected by the cornea is further reflected by the half mirror 40, as it is, on the same optical axis $O_O$ as the illumination light of the XY alignment light source 54 to be led to the XY alignment sensor 56.

Figure 4:
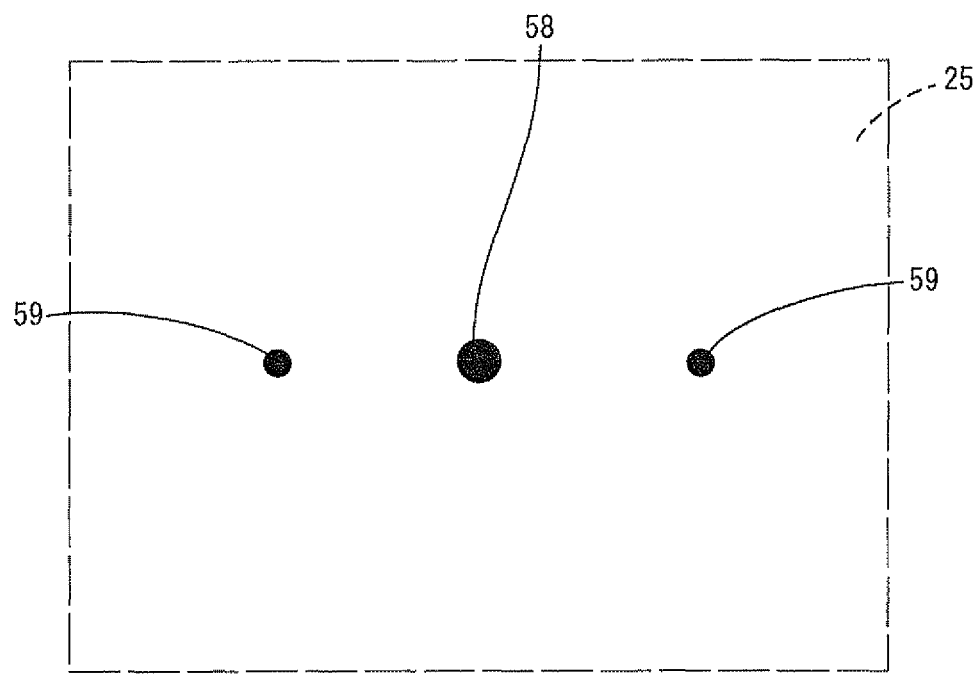
FIG. 4 is an illustrative drawing for explaining an alignment luminance point for alignment and kerato-ring luminance points displayed on a display monitor.

Also, in front of the eye under examination E, two kerato-ring light sources 57, 57 are provided on both sides of the optical axis $O_O$ of the XY alignment light source 54. These kerato-ring light sources 57, 57 emit infrared light beams, each of which passes through a pinhole and a project lens, not shown, and turns into parallel light fluxes to be projected on the cornea of the eye under examination E. Then, the light beam from the XY alignment light source 54 and the light beams from the kerato-ring light sources 57, 57 are reflected by the cornea to form respective images on the observation CCD 42 as an alignment luminance point 58 and kerato-ring luminance points 59, 59, as shown in FIG. 4. The alignment luminance point 58 and kerato-ring luminance points 59, 59 are positioned in such a way that the alignment luminance point 58 appears at the center and the kerato-ring luminance points 59, 59 appear on the left and right thereof. In other words, the cornea imaging apparatus 10 of the present embodiment is integrated with a keratometer 60 comprising the fixation target optical system 28, XY alignment illumination optical system 50, and the kerato-ring light sources 57, 57.

The specular optical system 32 is configured to include an illumination optical system 62 and a cornea imaging optical system 64. The illumination optical system 62 is configured to be provided with, in the following order from the position nearest the eye under examination E, a projection lens 66, a cold mirror 68, a slit 70, a condenser lens 72, and an illumination light source 74. As the illumination light source 74, an LED or the like that emits a flux of visible light is used. The cold mirror 68 is made to let infrared light through but reflect visible light. Then the light flux emitted from the illumination light source 74 passes though the condenser lens 72 and the slit 70 to become a slit light flux and is reflected by the cold mirror 68 before entering into the cornea of the eye under examination E in a diagonal direction through the projection lens 66.

The cornea imaging optical system 64 is configured to be provided with, in the following order from the point nearest the eye under examination E, an object lens 76, a cold mirror 78, and an imaging CCD 80 as a photoelectric element. Then, the slit light flux emitted from the illumination light source 74 and is reflected by the cornea of the eye under examination E is further reflected by the cold mirror 78 through the object lens 76 to form an image on the imaging CCD 80.

The optical axis $O_L$ of the illumination optical system 62 and the optical axis $O_P$ of the cornea imaging optical system 64 are set to intersect with each other at a given angle α. Then, the bisector of the angle α created by the optical axis $O_L$ of the illumination optical system 62 and the optical axis $O_P$ of the cornea imaging optical system 64 is considered to be the imaging center axis Os of the specular optical system 32. Also, the intersection point between the optical axis $O_L$ of the illumination optical system 62 and the optical axis $O_P$ of the cornea imaging optical system 64 is considered to be the focal position Pc of the specular optical system 32.

Furthermore, the specular optical system 32 is provided with a Z-alignment illumination optical system 82 that aligns part of its optical axis with the optical axis $O_P$ of the cornea imaging optical system 64 and a Z-alignment detection optical system 84 that aligns part of its optical axis with the optical axis $O_L$ of the illumination optical system 62. The Z-alignment illumination optical system 82 is configured to be provided with, in the following order from the point nearest the eye under examination, an object lens 76, a cold mirror 78, and a Z-alignment light source 86. As the Z-alignment light source 86, infrared light source such as an infrared LED, for example, is preferably used. Then, a flux of infrared light emitted from the Z-alignment light source 86 is irradiated diagonally onto the cornea. The Z-alignment light source 86 can also be configured by combining, for example, a visible light source such as a halogen lamp or a visible light LED, with an infrared filter. However, the Z-alignment light source 86 does not necessarily have to be an infrared light source, but can be a visible light source such as a halogen lamp or a visible LED. In case of using a visible light source, the luminance is preferably made smaller than that of the illumination light source 74. This allows the burden imposed on the test subject to be lightened during an alignment step or the like upon irradiation of a flux of light from the Z-alignment light source 86 onto the eye of the test subject.

The Z-alignment detection optical system 84 is configured to be provided with, in the following order from the point nearest the eye under examination E, the projection lens 66, the cold mirror 68 and a line sensor 88. Then, it is made in such a way that a flux of light emitted from the Z-alignment light source 86 and reflected by the cornea of the eye under examination E passes through the projection lens 66 and cold mirror 68 to form an image on the line sensor 88.

Figure 5:
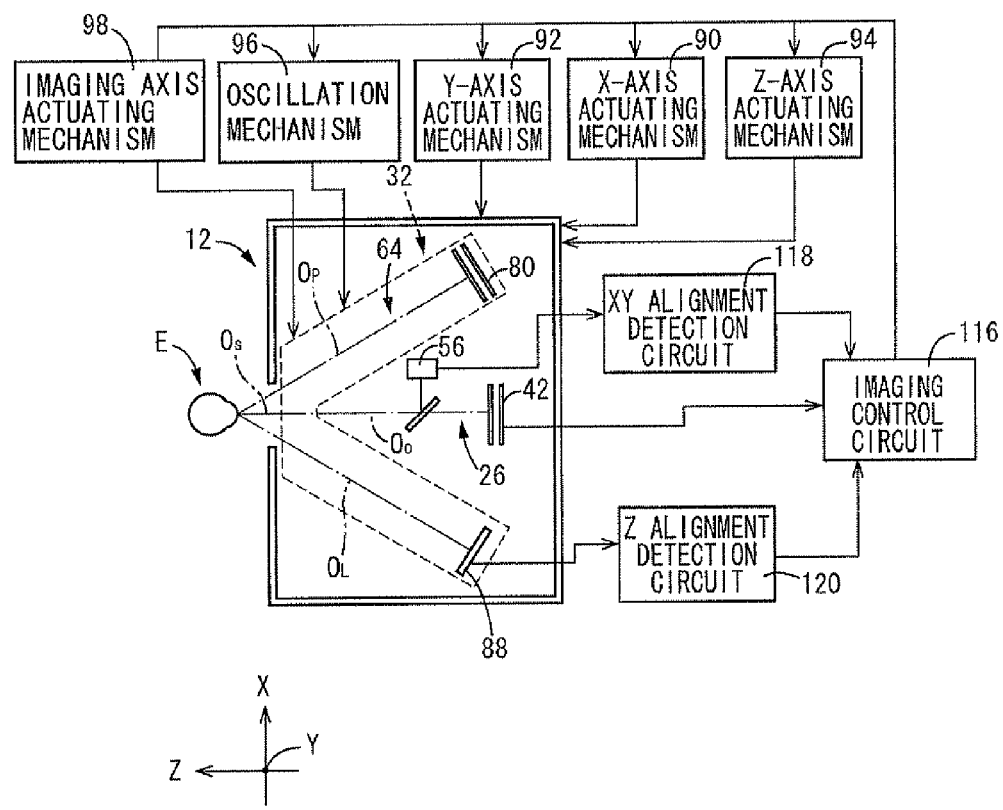
FIG. 5 is an illustrative drawing for explaining a control circuit and the like to be connected to the optical system shown in FIG. 1.

Furthermore, as shown in FIG. 5, the cornea imaging apparatus 10 is provided with an actuating means that moves the instrumental optical system 12 in the direction closer to, or away from the eye under examination E. Such actuating means is composed of a rack pinion mechanism, for example, and provided, in the present embodiment, with an X-axis actuating mechanism 90 that moves the instrumental optical system 12 in the horizontal X direction (up-down direction in FIG. 5) perpendicular to the direction of getting closer to or away from the eye under examination E, a Y-axis actuating mechanism 92 that moves the same in the Y direction (perpendicular to the printed surface in FIG. 5) extending vertically, and a Z-axis actuating mechanism 94 that moves the same in the Z direction (along the optical axis $O_O$ of the observation optical system 26, right-left direction in FIG. 5) extending horizontally getting closer to or away from the eye under examination E. Then, in the present embodiment, the X-direction actuating means is configured to comprise the X-axis actuating mechanism 90 and the imaging axis actuating mechanism 98 described later. Also, the Y-direction actuating means is configured to comprise the Y-axis actuating mechanism 92. In addition, the Z-direction actuating means is configured to comprise the Z-axis actuating mechanism 94 and the imaging axis actuating mechanism 98 described later.

Moreover, the cornea imaging apparatus 10 is provided with an oscillation mechanism 96 that particularly oscillates only the specular optical system 32 within the instrumental optical system 12, and an imaging axis actuating mechanism 98 as an imaging direction actuating means that moves only the specular optical system 32 on the imaging center axis Os. As schematically shown in FIGS. 2 and 3, the illumination optical system 62 and Z-alignment detection optical system 84 partially sharing the same optical axis are installed on a support table 100a, whereas the cornea imaging optical system 64 and Z-alignment illumination optical system 82 partially sharing the same optical axis are installed on a support table 100b in the specular optical system 32. These support tables 100a and 100b are each made in a form of a longitudinal plate and arranged to form a V-shape with each longitudinal side directed along the optical axis $O_L$ of the illumination optical system 62 and the optical axis $O_P$ of the cornea imaging optical system 64, respectively.

The support tables 100a and 100b are arranged on a circular arc rail 102 to be integrally movable therewith. The circular arc rail 102 is in an arc form having the curvature center C on the side of the eye under examination E. The circular arc rail 102 is formed with a rack 104 that is meshed with a pinion 108 provided on an actuating axis of an electric motor 106 to configure a rack pion mechanism. With this arrangement, when the electric motor 106 is actuated, the circular arc rail 102 oscillates around the center C as an oscillation center allowing only the specular optical system 32 to be oscillated in the circumferential direction of the eye under examination E around the oscillation center C without moving the fixation target optical system 28. As a result, under a state where the collimation axis of the eye under examination E is fixed straight ahead by means of the fixation target optical system 28, the imaging center axis Os of the specular optical system 32 is inclined against the front-sight axis O of the eye under examination E that is aligned with the optical axis $O_O$ of the fixation target optical system 28 to adjust the rotation of the pinion 108 so that the inclination angle of the imaging center axis Os can be changed relative to the front-sight axis O. Thus, the support tables 100a, 100b, circular arc rail 102, electric motor 106, and pinion 108 constitute the oscillation mechanism 96, which in turn constitutes the inclination angle changing means.

The curvature center C of the circular arc rail 102 that makes the oscillation center of the specular optical system 32 is preferably set at or near the curvature center of the corneal epithelium or corneal endothelium of the eye under examination E. Also, the curvature value of the circular arc rail 102 is preferably set in proximity to that of the corneal epithelium or endothelium of the eye under examination E. Furthermore, the value of the central angle of the circular arc rail 102 is set at a level whereby the imaging center axis Os of the specular optical system 32 can move over the entire imaging area of the corneal endothelium.

In addition, on each opposing surface of the support tables 100a and 100b on the side of the eye under examination E, a rack 110a and a rack 110b are formed, respectively, extending in the direction of the imaging center axis Os. On the circular arc rail 102, a pair of pinions 114a, 114b meshed with each other, one of which is installed on the actuating axis of an electric motor 112 are provided, and these pinions 114a, 114b are meshed with the racks 110a, 110b of the support tables 100a, 100b to constitute the rack pinion mechanism. With this arrangement, when the electric motor 112 is actuated, the support tables 100*a*, 100*b* move back and forth on the circular arc rail 102 in the direction of the imaging center axis Os. As a result, the illumination optical system 62 and cornea imaging optical system 64 provided on the support tables 100*a*, 100*b* are moved in the direction of the imaging center axis Os to shift the position of the focal position Pc, that is an intersection between an optical axis $O_L$ of the illumination optical system 62 and the optical axis $O_P$ of the cornea imaging optical system 64, on the imaging center axis Os in a direction of getting closer to or away from the eye under examination E. Thus, the support tables 100*a*, 100*b*, electric motor 112, and pinions 114*a*, 114*b* constitute the imaging axis actuating mechanism 98.

As evident from FIG. 3, as to the mirror 34 and mirror 36 that constitute the fixation target optical system 28, the mirror 34 is arranged above the support tables 100*a*, 100*b*, whereas the mirror 36 is arranged under the same. This allows the mirror 34 and mirror 36 to reflect light along the optical axis $O_O$ of the fixation target optical system 28 downward from the support tables 100*a*, 100*b*. As a result, various parts such as the half mirrors 38, 40 that constitute the fixation target optical system 28, observation optical system 26, and XY alignment optical system 30 and the like as well as the fixation target light source 48 and observation CCD 42 are arranged under the support tables 100*a*, 100*b* so as not to interfere with the oscillation thereof. Thus, the mirror 34 and mirror 36 make up an optical axis height changing means.

Also, the control unit 14 of the cornea imaging apparatus 10 (see FIG. 1) comprises printed circuit boards and the like provided with a CPU, a ROM, and a RAM, for example. In the control unit 14, an imaging control circuit 116 as an imaging control means that controls the operation of imaging the cornea with the instrumental optical system 12. The X-axis actuating mechanism 90, Y-axis actuating mechanism 92, Z-axis actuating mechanism 94, oscillation mechanism 96, and imaging axis actuating mechanism 98 are each connected to the imaging control circuit 116 to be actuated by an actuation signal from the imaging control circuit 116. Also, the XY alignment sensor 56 is connected to an XY alignment detection circuit 118, which is in turn connected to the imaging control circuit 116. Also, the line sensor 88 is connected to a Z alignment detection circuit 120, which is in turn connected to the imaging control circuit 116. This enables the information detected by the XY alignment sensor 56 and the line sensor 88 to be inputted to the imaging control circuit 116. Although omitted in the drawings, the imaging control circuit 116 is also connected to each of light sources 44, 74, 86, 48, 54 and 57, and is able to control their emission.

Figure 6:
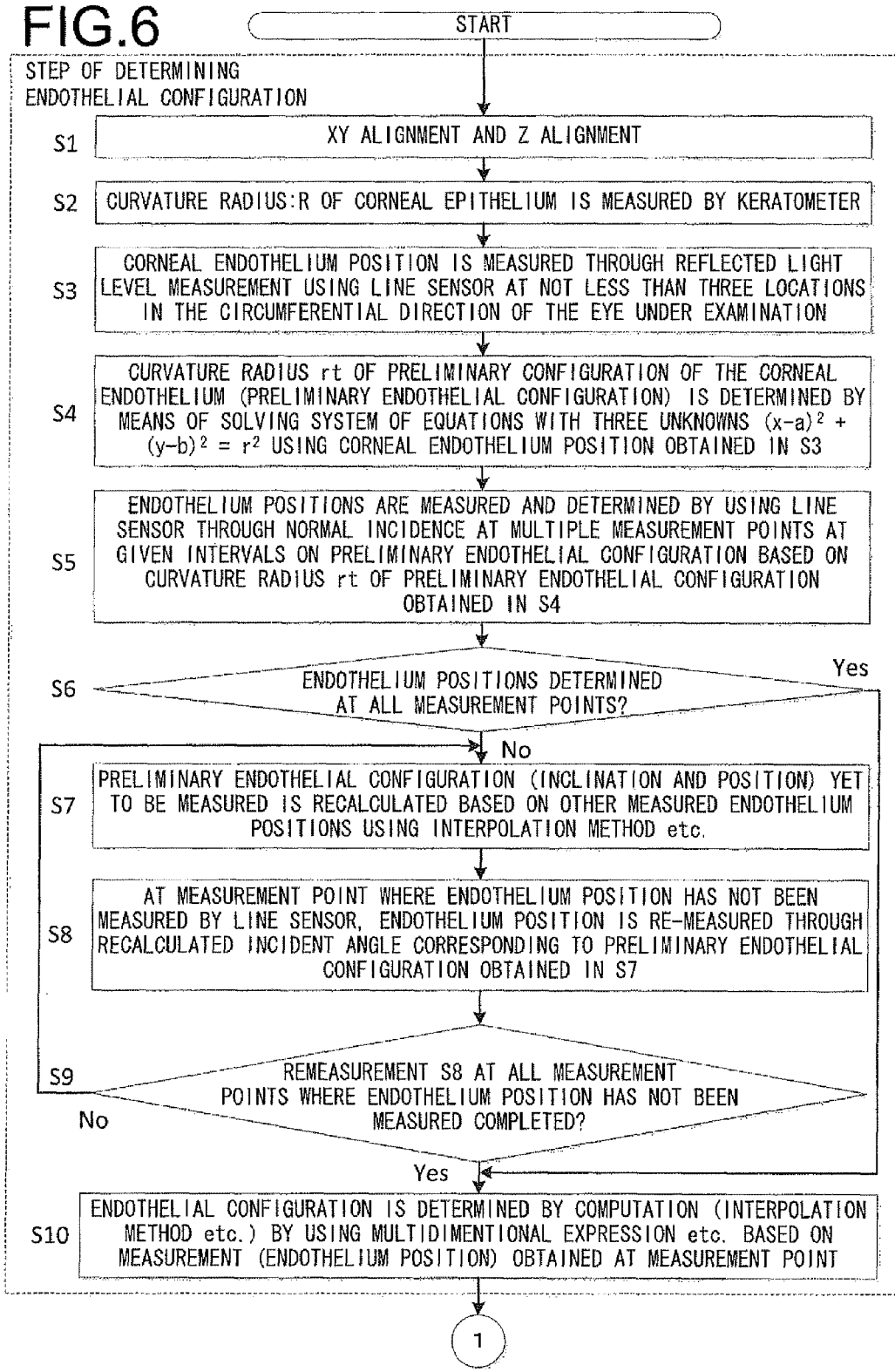
FIG. 6 is a flow chart showing a step of determining an endothelial configuration of a cornea imaging method as the first embodiment of the present invention.
Figure 7:
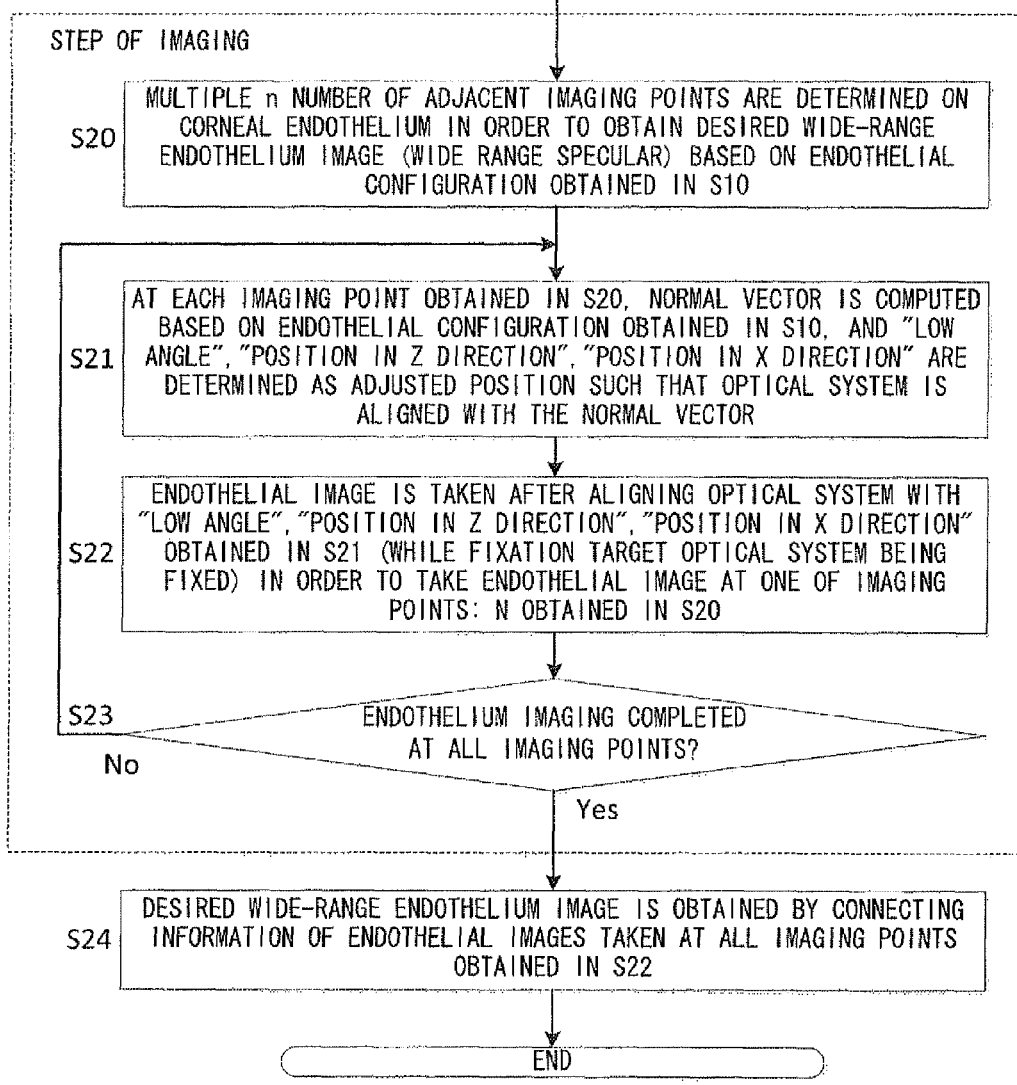
FIG. 7 is a flow chart showing a step of imaging of the cornea imaging method as the first embodiment of the present invention.

Next, FIGS. 6 and 7 show schematic flow charts of steps involved in imaging the cornea as one embodiment of the present invention related to the cornea imaging method performed by the imaging control circuit 116 in the cornea imaging apparatus 10 structured as above, which will be described one by one below. The process of imaging the corneal endothelium is broadly divided into a step of determining the endothelial configuration shown in FIG. 6 and a step of imaging shown in FIG. 7.

Figure 8:
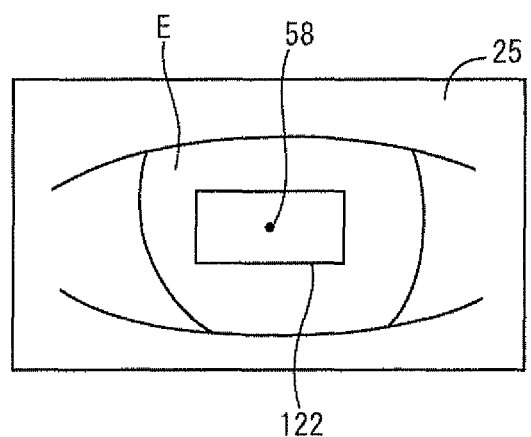
FIG. 8 is an illustrative drawing for explaining an eye under examination displayed on the display monitor.

In the step of determining the endothelial configuration shown in FIG. 6, positioning of the instrumental optical system 12 (XY alignment and Z alignment) is first performed relative to the eye under examination E in S1. During the XY alignment, the fixation target light emitted from the fixation target light source 48 is irradiated onto the eye under examination E. Then, by having the test subject fixate such fixation target light, the collimation direction of the eye under examination E can be retained in a state of front viewing aligned with the direction of the optical axis $O_O$ of the observation optical system 26. Under such a state, light fluxes emitted from the observation light sources 44, 44 and reflected at the front portion of the eye under examination E are led to the observation CCD 42. This allows the front portion of the eye under examination E to be displayed on the display monitor 25 as shown in FIG. 8.

Additionally, on the display monitor 25, an alignment pattern 122 in a shape of a rectangular frame generated by superimposed signals, for example, is displayed overlapping with the eye under examination E. At the same time, the light flux emitted from the XY alignment light source 54 toward the eye under examination E is reflected at the front portion thereof and led to the observation CCD 42 to be displayed on the display monitor 25 as the spot-shaped alignment luminance point 58. Then, the operator can actuate the instrumental optical system 12 by means of operating the operation stick 16 for adjusting the position of the instrumental optical system 12 to keep the alignment luminance point 58 within the alignment pattern 122.

Also, part of the light flux emitted from the XY alignment light source 54 and reflected at the front portion (corneal epithelium) of the eye under examination E is reflected by the half mirror 40 to be led to the XY alignment sensor 56. The burden imposed on the test subject is alleviated by using an infrared light flux not recognized by the test subject emitted from the XY alignment light source 54. Here, the XY alignment sensor 56 is made to be capable of detecting the positions of the alignment luminance point 58 in X and Y directions once it enters into the frame of the alignment pattern 122. Such positions in X and Y directions are inputted to the XY alignment detection circuit 118. The XY alignment detection circuit 118 actuates the X-axis actuating mechanism 90 to bring the optical axis $O_O$ of the observation optical system 26 closer to the collimation axis of the eye under examination E based on the information on the position of the alignment luminance point 58 in the X direction, while actuating the Y-axis actuating mechanism 92 to bring the optical axis $O_O$ of the observation optical system 26 closer to the collimation axis of the eye under examination E based on the information on the position of the same in the Y direction. This allows the instrumental optical system 12 to be positioned against the eye under examination E in the X and Y directions.

Especially in the present embodiment, the XY alignment light source 54 and the observation light sources 44, 44 are made to flash alternately in short time while the detection by the XY alignment sensor 56 is performed in line with the timing of the flashing of the XY alignment light source 54 when the observation light sources 44, 44 are turned off. This prevents the infrared light flux of the observation light sources 44, 44 from affecting the XY alignment. Since the flashing speeds of the XY alignment light source 54 and the observation light sources 44, 44 are greater than the speed of conversion into the light receiving signals in the observation CCD 42, no flashing of the light sources 54, 44 is recognized on the display monitor 25 to which the light receiving signals of the observation CCD 42 are outputted, making it look as though the light sources 54, 44 are continuously lit.

Also, the Z-alignment adjusts the position of the instrumental optical system 12 in the Z direction so as to allow the line sensor 88 to receive the light flux emitted from the Z-alignment light source 86 and reflected by the cornea of the eye under examination E and to allow the observation CCD 42 to image the light flux emitted from the kerato-ring light sources 57, 57 and reflected by the cornea of the eye under examination E by means of actuating the Z-axis actuating mechanism 94 and advancing the instrumental optical system 12 in the direction getting closer to the eye under examination E by a given distance.

Next in 52, the curvature of the corneal epithelium of the eye under examination E on a horizontal plane is measured using the keratometer 60. Since the known technology described in Japanese Unexamined Patent Publication No.JP-A-2007-215956, for example, is adoptable as the measurement method of the curvature of the corneal epithelium, only a brief description will be given hereinafter. First, two kerato-ring light sources 57, 57 are turned on under a state where the XY alignment light source 54 is turned on. Then, two kerato-ring luminance points 59, 59 are displayed on the display monitor 25 on the left and right sides of the alignment luminance point 58 as shown in FIG. 4 by having the light flux emitted from the kerato-ring light sources 57, 57 irradiated onto the eye under examination E and reflected by the cornea thereof to be led to the observation CCD 42. The curvature radius R of the corneal epithelium of the eye under examination E on a horizontal plane is determined by identifying, from the coordinate values of these kerato-ring luminance points 59, 59, the configuration of an approximate ellipse, that is, elliptic approximation of the corneal configuration. This way, the configuration of the corneal epithelium is determined, as shown in FIG. 9A.

Figure 9A:
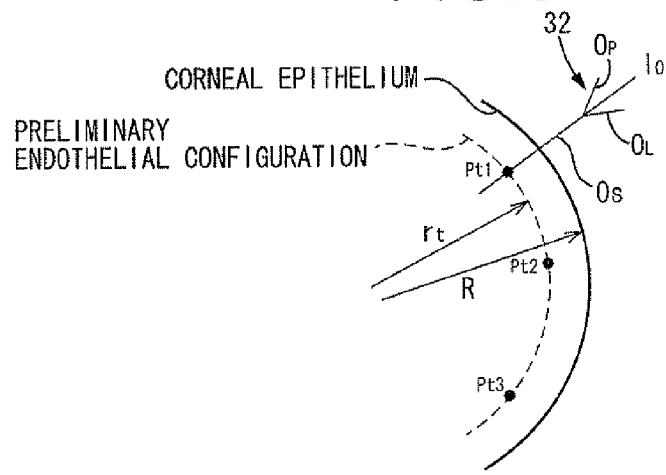
FIGS. 9A-9C are illustrative drawings for explaining in detail the step of determining the endothelial configuration shown in FIG. 6.

And in S3, the oscillation mechanism 96 is actuated based on the corneal epithelial configuration obtained from S2 to move the specular optical system 32 to a position where the imaging center axis Os gets aligned with the normal vector direction $1_O$ of the corneal epithelium as shown in FIG. 9A. Next, the Z-alignment light source 86 is turned on to emit an infrared light flux therefrom to direct it diagonally onto the cornea of the eye under examination E, and the light flux reflected by the cornea is received by the line sensor 88. Since the light flux irradiated from the Z-alignment light source 86 is an infrared light flux, especially in the present embodiment, the burden imposed on the test subject is alleviated.

Figure 10:
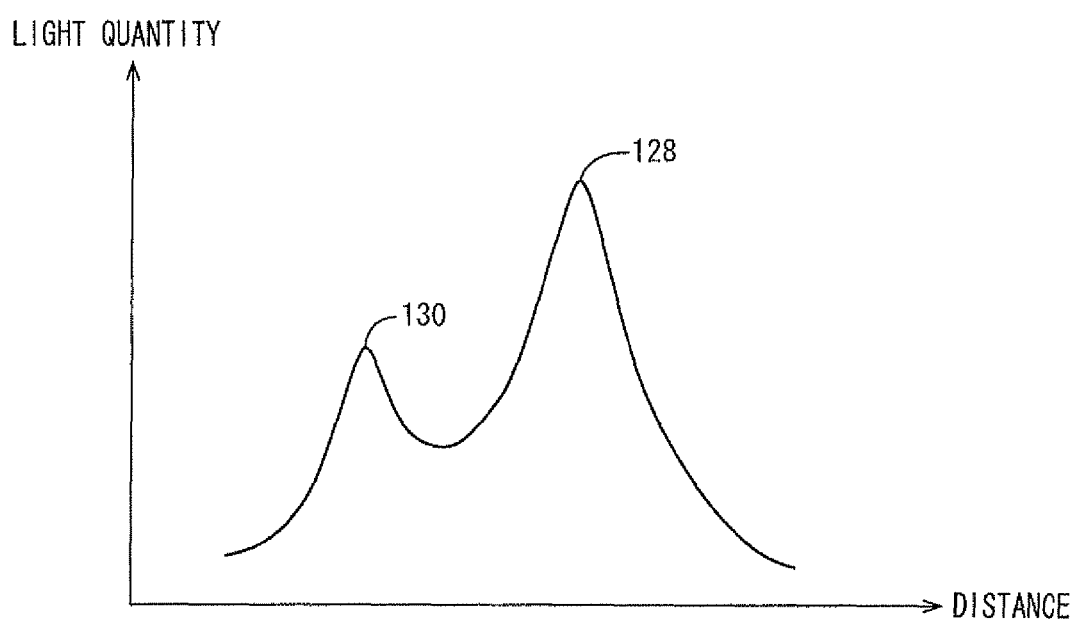
FIG. 10 is a graph showing an example of light quantity distribution of a light reflected from the cornea.

These reflected light fluxes are detected by the line sensor 88, which detects the light quantity distribution shown in FIG. 10. In FIG. 10, a first peak 128 indicating the greatest light quantity shows the light reflected from the corneal epithelium. Next, a second peak 130 indicating the second greatest light quantity shows the light reflected from the corneal endothelium. This allows point Pt1 of the corneal endothelium to be measured as shown in FIG. 9A. Then, the Z-axis actuating mechanism 94 and the oscillation mechanism 96 are actuated to measure such positions of the corneal endothelium at not less than three locations (three locations in this example) in the circumferential directions of the cornea by means of rotating only the specular optical system 32 in the circumferential direction of the eye under examination E keeping the collimation axis thereof fixed so as to determine preliminarily measured points Pt1 to Pt3 of the corneal endothelium.

Next, in S4, the curvature radius $r_t$ of the preliminary endothelial configuration shown in FIG. 9A, which is an interim configuration of the endothelium, is determined by means of solving a system of equations with three unknowns by a circle equation $(x-a)^2+(y-b)^2=r^2$ using the preliminarily measured points Pt1 to Pt3 of the corneal endothelium obtained in S3.

Figure 9B:
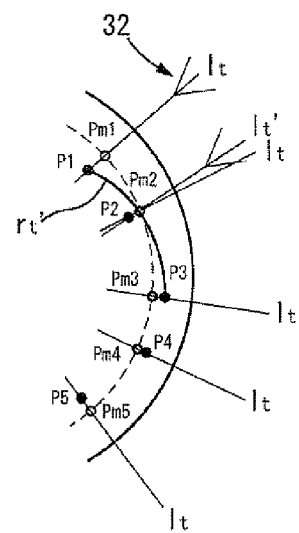

Next, in S5, multiple measurement points (5 locations in this example) Pm1 to Pm5 (marked with ○ in FIG. 9B) at given intervals are set in the circumferential direction on the preliminary endothelium based on the curvature radius $r_t$ of the preliminary endothelial configuration obtained in S4 as shown in FIG. 9B, and for each of these measurement points Pm1 to Pm5, the Z-axis actuating mechanism 94 and the oscillation mechanism 96 are actuated to move the specular optical system 32 to a position where the imaging center axis Os gets aligned with the normal vector direction $1_t$ of the preliminary endothelium at the measurement points Pm1 to Pm5. Then, as was done in S3, the infrared light flux emitted from the Z-alignment light source 86 and reflected by the cornea is received by the line sensor 88 to determine the measured positions P1 to P5 (marked with ● in FIG. 9B) in the normal vector direction $1_t$ of the preliminary endothelium at the measurement points Pm1 to Pm5 based on the light quantity distribution of the line sensor 88.

Next, in S6, it is judged whether the measured positions P1 to P5 of the corneal endothelium have been determined or not at each of the measurement points Pm1 to Pm5 based on the light quantity distribution of the line sensor 88, and in case the positions P1 to P5 of the corneal endothelium are yet to be measured (S6 is No) at any of the measurement points Pm1 to Pm5, a preliminary configuration (inclination and position) $r_t'$ of the corneal endothelium (shown by a solid line in FIG. 9B) is recalculated in S7 at measurement point Pmt yet to be measured based on the measured positions P1, P3, P4 and P5 using an interpolation method such as the Lagrange interpolation or spline interpolation as exemplified in FIG. 9B that shows a situation where point P2 is yet to be measured. Then, in S8, a normal vector direction $1_t'$ relative to the obtained preliminary endothelial configuration $r_t'$ is recalculated at the measurement point Pm2 where the corneal endothelium position has not been measured so as to re-measure the measurement point P2 of the corneal endothelium, on the normal vector direction $1_t'$ thereof at the measurement point Pm2 using the line sensor 88, by means of actuating the Z-axis actuating mechanism 94 and the oscillation mechanism 96 and aligning the imaging center axis Os of the specular optical system 32 with the recalculated normal vector direction $1_t'$.

Figure 9C:
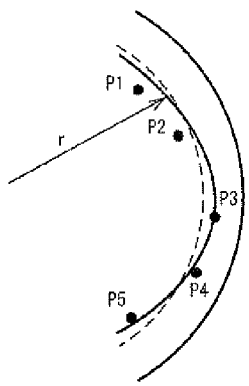

Then, in case of having obtained the measured positions P1 to P5 of the corneal endothelium at all measurement points Pm1 to Pm5 (S6 is Yes, or 59 is Yes), the corneal endothelial configuration r (shown by a solid line in FIG. 9C) between the measured positions P1 to P5 is determined by computation in S10, as shown in FIG. 9C, from the obtained measured positions P1 to P5 of the corneal endothelium using an interpolation method such as the Lagrange interpolation, spline interpolation or hyperbolic functions. This way, the step of determining the endothelial configuration is complete. As described above, in the present embodiment, the endothelial configuration computing means comprises the line sensor 88 and the control unit 14, and the endothelial configuration computing step comprises the steps S2 to S10.

Figure 11A:
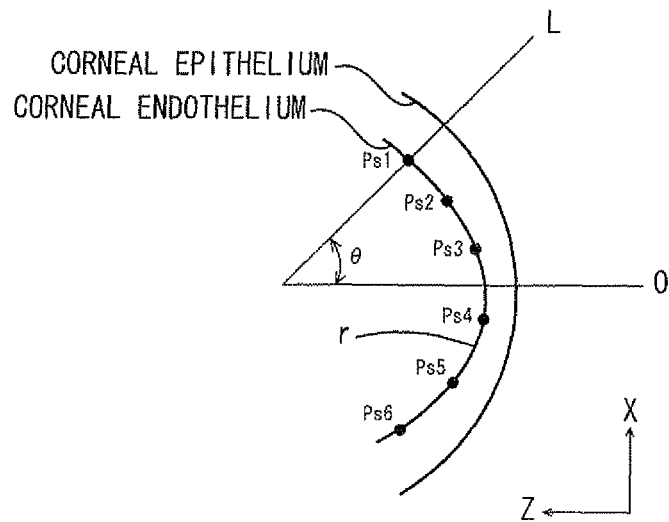
FIGS. 11A and 11B are illustrative drawings for explaining in detail the step of imaging shown in FIG. 7.

Subsequently, the step of imaging shown in FIG. 7 is implemented. First, in S20, multiple "n" number (n=6 in this example) of imaging points Ps1 to Ps6 are determined on the corneal endothelium in the circumferential direction of the eye under examination E from the corneal endothelial configuration obtained in S10 as shown in FIG. 11A. Among the imaging points Ps1 to Ps6, two adjacent ones are preferably set within a distance that can be covered by a single endothelial image to be able to generate a wide range image of the endothelium (wide range specular) by connecting the endothelial image at each of the imaging points Ps1 to Ps6 as described later.

Next, steps S21 and S22 are implemented for each of the imaging points Ps1 to Ps6. Describing in reference to the imaging point Ps1, for example, a normal vector L of the corneal endothelium at the imaging point Ps1 is first computed in S21 based on the endothelial configuration r obtained in S10, as shown in FIG. 11A. Then, a low angle θ, which is the inclination angle of the normal vector L against the front-sight axis O of the eye under examination E and the positions of the imaging point Ps1 in the X and Z directions are determined. Thus, in the present embodiment the normal vector computing means for the endothelium comprises the control unit 14, whereas the normal vector computing step for the endothelium comprises S21.

Figure 11B:
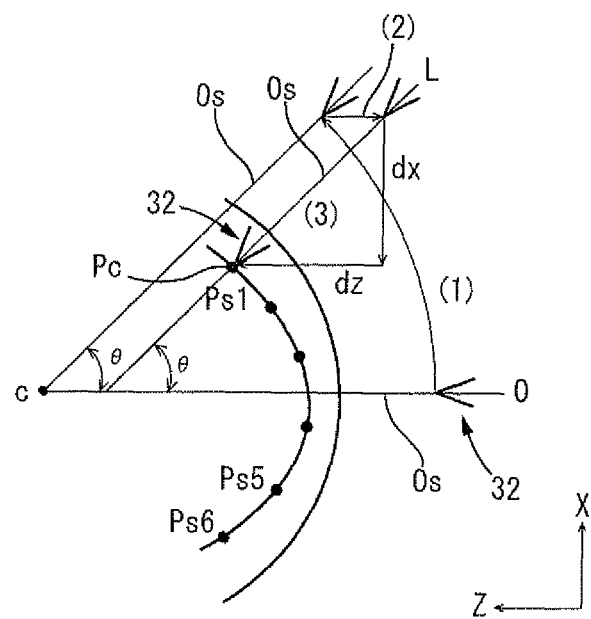

And in S22, the position of the specular optical system 32 is aligned with the imaging position of the imaging point Ps1, as shown in FIG. 11B. The imaging position of the imaging point Ps1 means a position where the specular optical system 32 has its imaging center axis Os aligned (coincided) with the normal vector L of the corneal endothelium at the imaging point Ps1, and at the same time, the focal position Pc is positioned at the imaging point Ps1.

First, in the present embodiment, (1) the inclination angle of the imaging center axis Os against the front-sight axis O is set at the low angle θ obtained in S21 to align it with the direction of the normal vector L (making the imaging center axis Os parallel to the normal vector L) by means of actuating the oscillation mechanism 96 keeping the fixation target optical system 28 and the observation optical system 26 fixed and rotating the imaging center axis Os of the specular optical system 32 around the oscillation center C under a state where the collimation axis of the eye under examination E is fixed straight ahead by means of the fixation target optical system 28. Next, (2) The Z-axis actuating mechanism 94 is actuated to align the imaging center axis Os with the normal vector L (making the imaging center axis Os coincide with the normal vector L). This alignment of the imaging center axis Os with the normal vector L can also be done by actuating the X-axis actuating mechanism 90 and moving the imaging center axis Os in the X direction. Then, (3) the imaging axis actuating mechanism 98 is actuated and the specular optical system 32 is moved in the direction of the imaging center axis Os by distances dx and dz in the X and Z directions, respectively, so as to bring the focal position Pc of the specular optical system 32 to the imaging point Ps1 aligning them with each other. Thus, in the present embodiment, it is made possible to move the specular optical system 32 simultaneously in the X and Z directions by actuating the imaging axis actuating mechanism 98 and moving the specular optical system 32 on the imaging center axis Os, and the X-direction actuating means that moves the specular optical system 32 in the X direction comprises the imaging axis actuating mechanism 98 and the X-axis actuating mechanism 90, whereas the Z-axis actuating means that moves the specular optical system 32 in the Z direction comprises the imaging axis actuating mechanism 98 and the Z-axis actuating mechanism 94. In summary, the imaging axis actuating mechanism 98 is capable of moving the specular optical system 32 simultaneously in the X and Z directions, and once the imaging center axis Os is aligned with the normal vector L, the specular optical system 32 can be moved with the imaging axis actuating mechanism 98 by a distance of dx in the X direction and a distance of dz in the Z direction by means of moving it in the direction of imaging center axis Os, or it can be moved by dz in the Z direction using the Z-axis actuating mechanism 94 after moving it by dx in the X direction with the X-axis actuating mechanism 90, and thus, the position of the specular optical system 32 in the X and Z directions can be adjusted by any combination of these imaging axis actuating mechanism 98, X-axis actuating mechanism 90, and Z-axis actuating mechanism 94. Moving the specular optical system 32 to the imaging position in such way does not have to be performed in the above sequence, but it can be done in a different order of sequence as long as the specular optical system 32 ultimately reaches the imaging position, and since each moving distance of the mechanisms 96, 94 (90) and 98 is already known, the above steps (1), (2) and (3) can be carried out simultaneously. Thus, in the present embodiment, the step S22 constitutes the position adjusting step of the imaging mechanism.

Then, conical endothelial images are taken at the imaging point Ps1 by turning on the illumination light source 74 and directing the light flux emitted therefrom diagonally onto the corneal endothelium of the eye under examination E while receiving the light flux reflected from the corneal endothelium by the imaging CCD 80.

Figure 12:
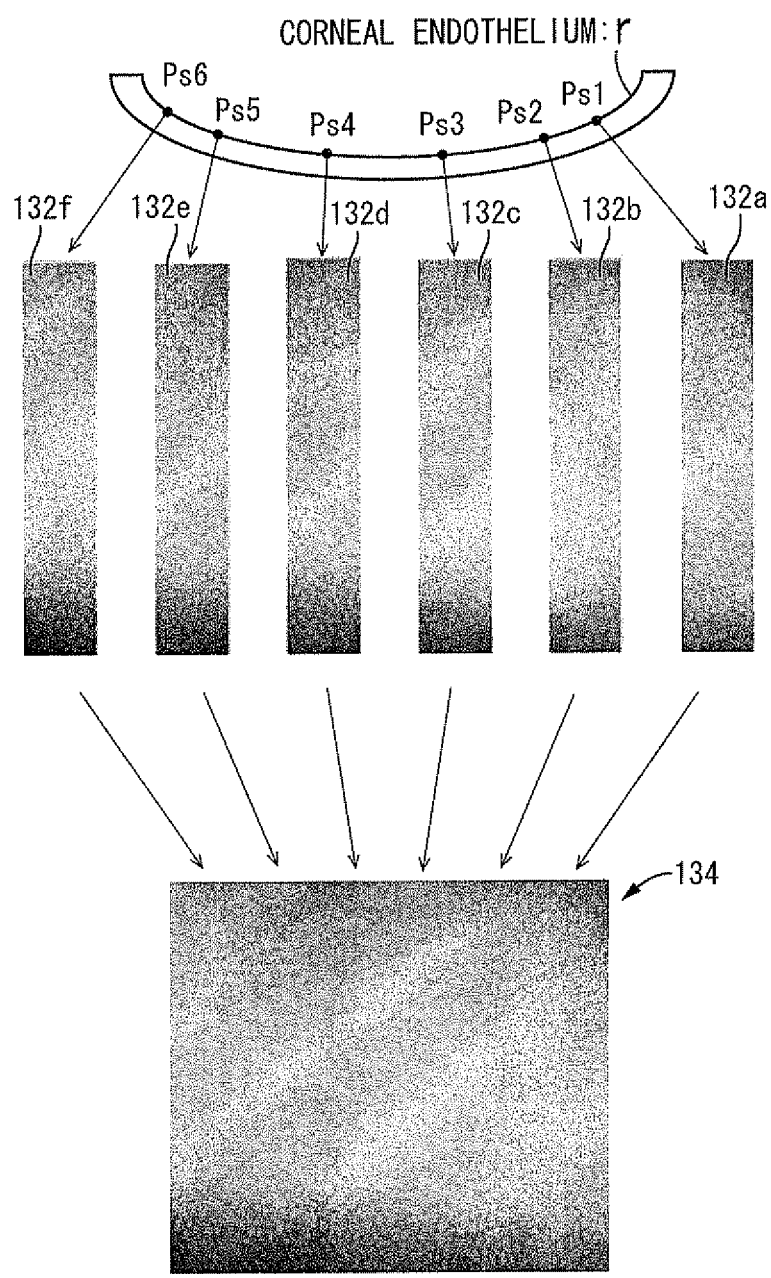
FIG. 12 is an illustrative drawing exemplifying an endothelium image and a wide-range endothelium image obtained from the step of imaging shown in FIG. 7.

Subsequently, in S23, the above steps S21 and S22 are performed consecutively until the image taking is complete at each of the imaging points Ps1 to Ps6. Thus, steps S21 to S23 constitute the consecutive imaging step. In taking consecutive images at the imaging points Ps1 to Ps6, imaging at each position can be performed under a state where the fixation target optical system 28 is fixed relative to the eye under examination E in the X and Y directions and the collimation axis of the eye under examination E is fixed by means of performing the alignment of the imaging center axis Os of the specular optical system 32 with the normal vector L (see (2) of FIG. 11B) by actuating the Z-axis actuating mechanism 94 and moving the instrumental optical system 12 in the Z direction. This makes it possible, as shown in FIG. 12, to obtain corneal endothelium images 132a to 132f at each of the imaging points Ps1 to Ps6. Once the image taking is complete at each of the imaging points Ps1 to Ps6, a wide-range endothelium image (wide range specular) 134 can be obtained in S24 by applying image processing to the corneal endothelium images 132a to 132f obtained at each of the imaging points Ps1 to Ps6 and connecting them with each other. Various methods can be adopted as appropriate for connecting the corneal endothelium images 132a to 132f, a method being, for example, such that edges of the endothelium images 132a to 132f are simply connected to each other, or the most closely correlated portions among the edges of the endothelium images 132a to 132f are considered the same position on the corneal endothelium and are overlapped with each other to be spliced at said position. Also, in the present embodiment, the imaging points Ps1 to Ps6 are set in a wide range over nearly the entire corneal endothelium to obtain the wide-range endothelium image 134 of almost the entire corneal endothelium, but there is no need for covering the entire area, and images can be taken consecutively within a limited distance of 1 to 2 mm from each other in the circumferential direction, for example, which can reduce the time to complete the imaging. The step of imaging is now completed as described above.

According to the cornea imaging apparatus 10 and the method of imaging the cornea following the present embodiment, images of the corneal endothelium were taken in S21, by determining the normal vector L of the corneal endothelium and aligning the normal vector L with the imaging center axis Os of the specular optical system 32 using the oscillation mechanism 96, Z-axis actuating mechanism 94 (or X-axis actuating mechanism 90), and the imaging axis actuating mechanism 98. This enables a more accurate imaging of the corneal endothelial cells. Since alignment of the specular optical system 32 is based on the corneal endothelial configuration, clear images of corneal endothelial cells can be taken even on the corneal periphery or in the eye with an ocular disorder where the difference in curvature is significant between the corneal epithelium and corneal endothelium.

Particularly, in calculating the endothelial configuration, the calculation is based on the epithelium positions P1 to P5 measured with the line sensor 88. This makes it possible to get the endothelial configuration closer to the real one. As a result, the specular optical system 32 can be aligned with the corneal endothelium in high accuracy to obtain clear images of the corneal endothelial cells.

Also, the imaging center axis Os of the specular optical system 32 can be aligned with the normal vector L at a given position on the corneal endothelium by means of providing the X-axis actuating mechanism 90, Z-axis actuating mechanism 94 and oscillation mechanism 96 and separately adjusting the X and Z directions of the specular optical system 32 and the inclination angle of the imaging center axis Os relative to the front-sight axis O of the eye under examination E. This allows the imaging center axis Os to be surely aligned with the normal vector direction of the corneal endothelium even with a significant variation in the curvatures of the corneal epithelium and corneal endothelium.

Especially by means of moving only the specular optical system 32 in oscillation with the oscillation mechanism 96 without moving the fixation target optical system 28, images of the corneal endothelium of the test subject can be taken at multiple locations with his eye fixating at a point without moving the collimation axis to obtain the wide-range endothelium image 134. Furthermore, by providing the imaging axis actuating mechanism 98 that moves the specular optical system 32 in the direction of the imaging center axis Os, it is possible to align the specular optical system 32 with the imaging position by a simple control, while allowing movements thereof in X and Z directions simultaneously, thus enabling a quick position alignment.

Figure 13:
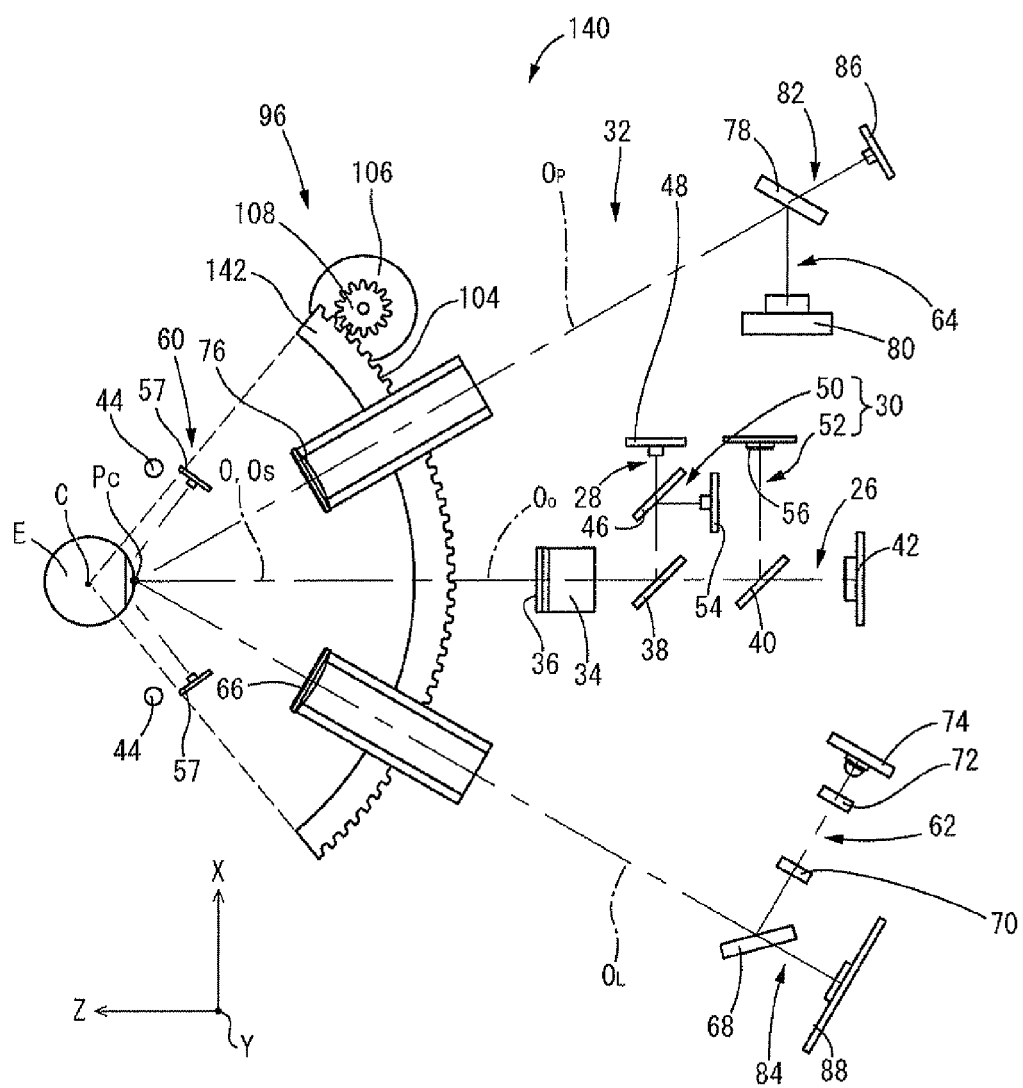
FIG. 13 is an illustrative drawing showing an upper view of an instrumental optical system as a second embodiment of the present invention.

Next, FIG. 13 shows a cornea imaging apparatus 140 as a second embodiment of the present invention. In the following paragraphs, the description of the parts with similar structures to those in the above first embodiment will be omitted by coding them in the drawings with the same numerals as those in the first embodiment.

The cornea imaging apparatus 140 according to the present embodiment has a structure in which a circular arc rail 142 is provided with the specular optical system 32 in a fixed way. That is, the cornea imaging apparatus 140 according to the present embodiment is without the imaging axis actuating mechanism 98 shown in FIG. 5 as opposed to the cornea imaging apparatus 10 of the above first embodiment. Therefore, the specular optical system 32 is capable of moving in the X direction by the X-axis actuating mechanism 90, in the Y direction by the Y-axis actuating mechanism 92, and in the Z direction by the Z-axis actuating mechanism 94 as well as oscillating around the oscillation center C by the oscillation mechanism 96.

Since the cornea imaging apparatus 140 with such structure adopts a similar configuration to that of the above first embodiment except for the movement of the specular optical system 32 to the imaging position as shown in S22 among those cornea imaging methods similar to that of the first embodiment shown in FIGS. 6 and 7, only processing procedures corresponding to S22 will be described hereinafter.

Figure 14:
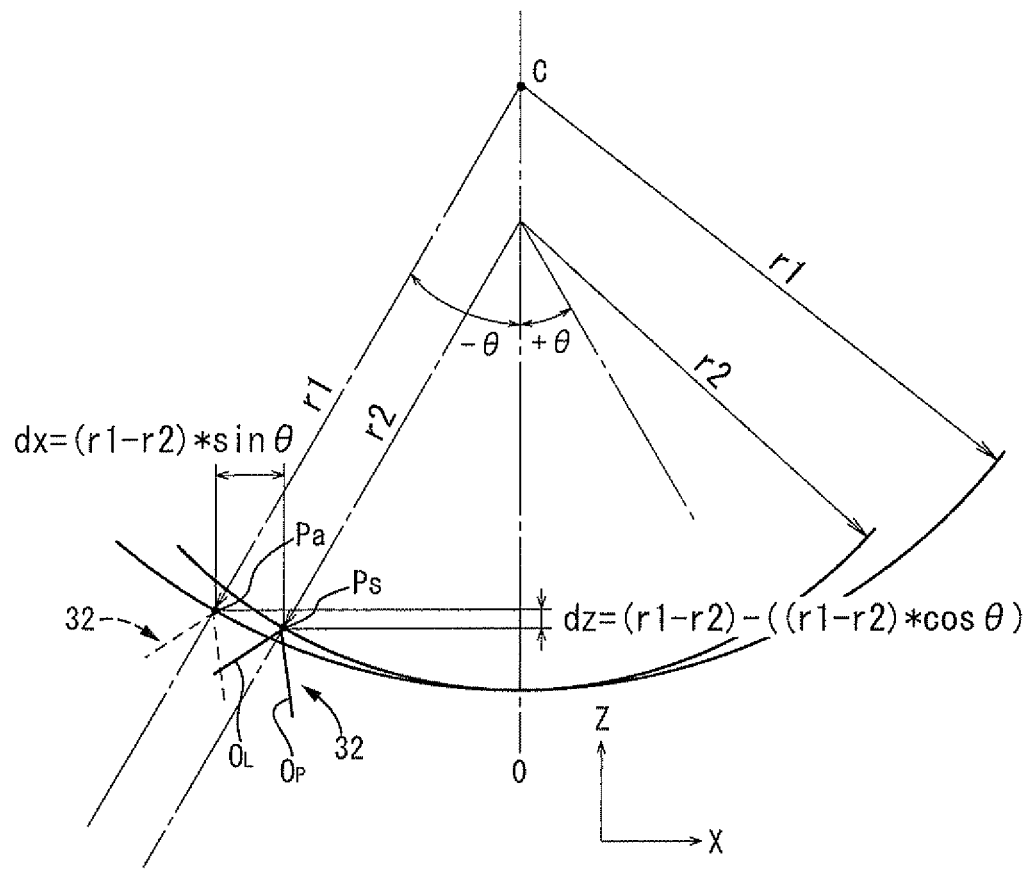
FIG. 14 is an illustrative drawing for explaining a positioning operation of the instrumental optical system shown in FIG. 13.

As shown in FIG. 14, when the specular optical system 32 is displaced in oscillation by the oscillation mechanism 96, the curvature radius r1 of the trajectory of the moving focal position Pc does not exactly coincide with the curvature radius r2 of the corneal endothelium. Therefore, the imaging center axis Os is aligned with the front-sight axis O of the eye under examination E by actuating the X-axis actuating mechanism 90 and the Z-axis actuating mechanism 94 to move the entire instrumental optical system 12 in X and Z directions as a preparation for moving the focal position Pc to the imaging point Ps. Next, the inclination angle of the imaging center axis Os against the front-sight axis O is set to the low angle −θ obtained in S21. This allows the focal position Pc of the specular optical system 32 to be positioned at Pa shown in FIG. 14.

Then, in order to move the focal position Pc from point Pa to the imaging point Ps, the X-axis actuating mechanism 90 and the Z-axis actuating mechanism 94 are actuated to move the instrumental optical system 12 by a distance dx in the X direction and a distance dz in the Z direction as given by the following equations:

$$dx=(r1-r2)*\sin\theta$$

$$dz=(r1-r2)-\{(r1-r2)*\cos\theta\}$$

This allows the specular optical system 32 to be positioned at the imaging point Ps.

Figure 15:
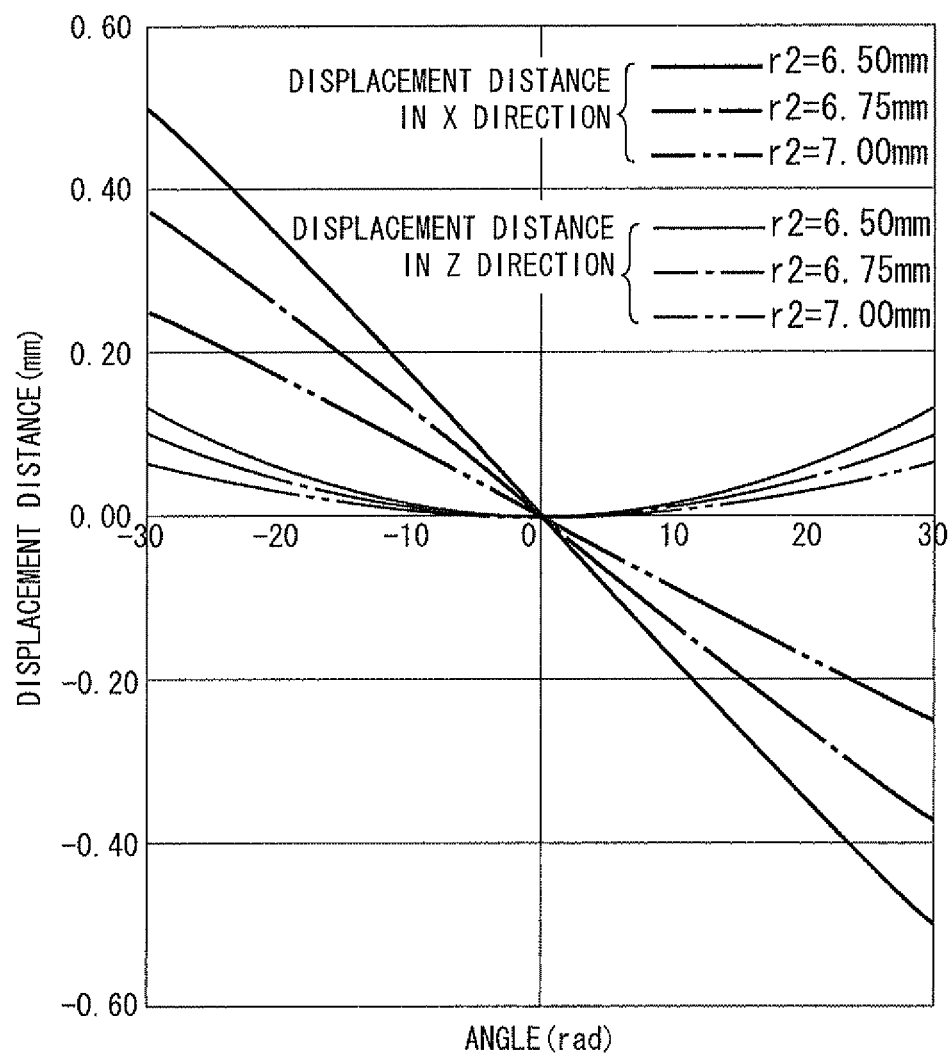
FIG. 15 is a graph showing an example of displacement distances of the X direction and Z direction for positioning to a specific location on the corneal endothelium having a given curvature radius.

The displacement distances dx and dz in the X and Z directions, respectively, can be calculated each time. Alternatively, necessary displacement distances dx and dz in the X and Z directions correspondent to the position of the imaging point Ps (rad) can be obtained from a data table as shown in FIG. 15 recorded in advance in the control unit 14. The data table contains the relationship between the position of the imaging point Ps on the corneal endothelium (curvature radius: r2) and the displacement distances dx and dz in X and Z directions, respectively, required to move the focal position to said imaging point Ps. Here, the position of the imaging point Ps is the angular position around the curvature center of the corneal endothelium (curvature radius: r2), i.e. −θ and θ (rad) shown in FIG. 14, assuming that the corneal apex equals zero. FIG. 15 shows required displacement distances in the X and Z directions when the curvature radius r1 of the trajectory of the moving focal position Pc equals 7.5 mm and the curvature radii of the corneal endothelium r2 are 6.5 mm, 6.75 mm and 7.0 mm.

According to the present embodiment, it is possible to accurately align the imaging center axis Os with the normal vector direction of various configurations of the corneal endothelium interpolated by hyperbolic functions, for example, because the specular optical system 32 is moved on a basis of the calculation results. Also, the same effect can be achieved with a simpler configuration since the imaging axis actuating mechanism 98 that moves the specular optical system 32 on the imaging center axis Os is not required, unlike the above first embodiment.

Figure 16:
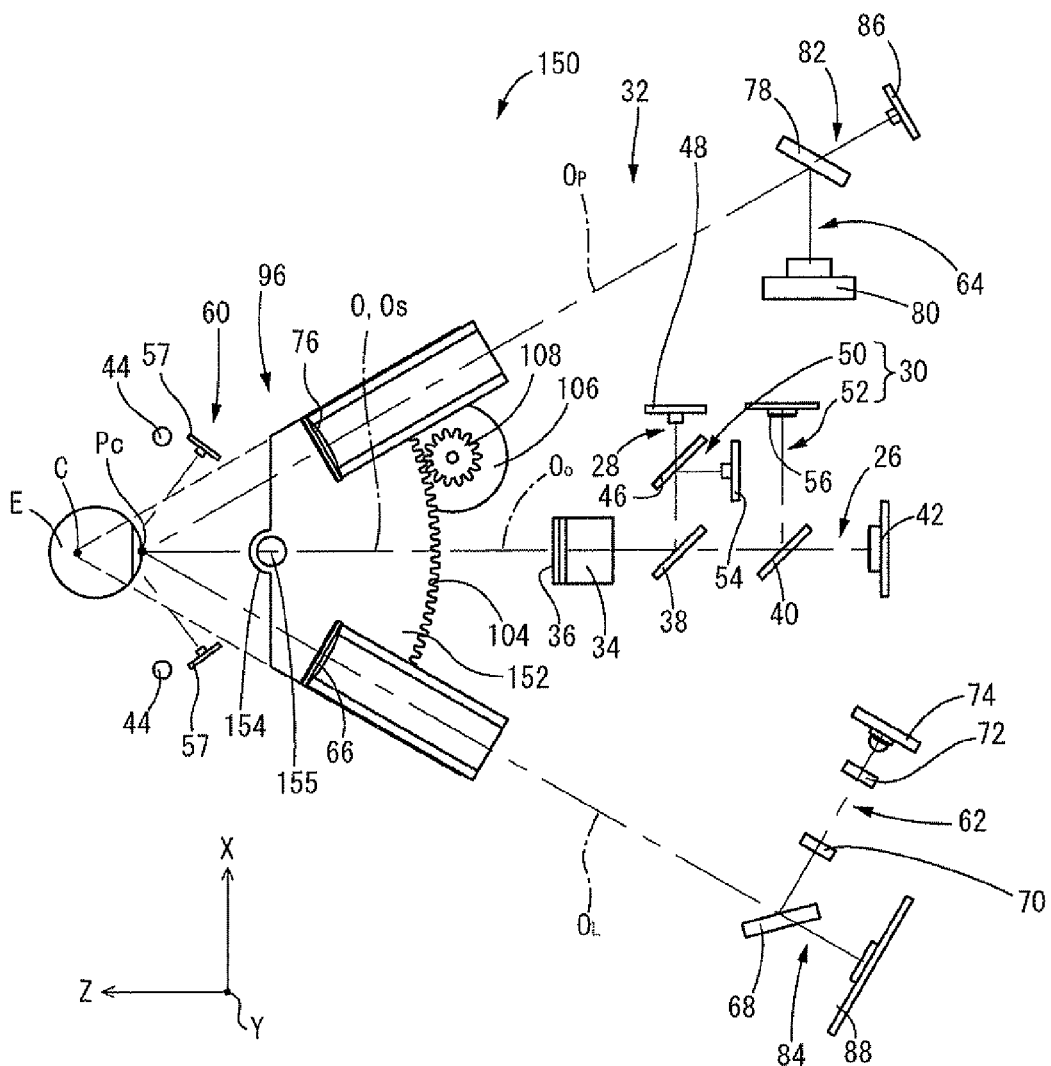
FIG. 16 is an illustrative drawing showing an upper view of an instrumental optical system as a third embodiment of the present invention.

Next, FIG. 16 shows a cornea imaging apparatus 150 as a third embodiment of the present invention. The cornea imaging apparatus 150 has a structure in which, like the cornea imaging apparatus 140 of the above second embodiment, a circular arc rail 152 is provided with the specular optical system 32 in a fixed way. The circular arc rail 152 of the present embodiment is in an approximate shape of a trapezoidal plate, the lower base of which at the edge is made into the rack 104 extending in a circular arc shape, which is meshed with the pinion 108 of the electric motor 106. Then, the edge of the upper base of the trapezoid on the other side from the rack 104 is provided with an axle 154 in a cylindrical form, and a rotatable shaft 155 provided protruding in the cornea imaging apparatus 150 is inserted into said axle 154 to make the shaft rotatable around it. Such cornea imaging apparatus 150 is capable of taking endothelial images as well as wide-range endothelial images following a cornea imaging method similar to that of the cornea imaging apparatus 140 of the second embodiment. According to the present embodiment, the circular arc rail 152 can securely support the optical parts such as the projection lens 66 and the object lens 76 that constitute the specular optical system 32 being in a shape of a plate that extends over a given area, thus enabling oscillation of the specular optical system 32 in a stable manner.

Each embodiment of the present invention was described in detail above, but the present invention is not limited to any such specific description thereof, but is rather implementable in different modes with various modifications, corrections and improvements, and needless to say, such embodiments are all within the range of the present invention as long as they do not deviate from the intention thereof.

Figure 17:
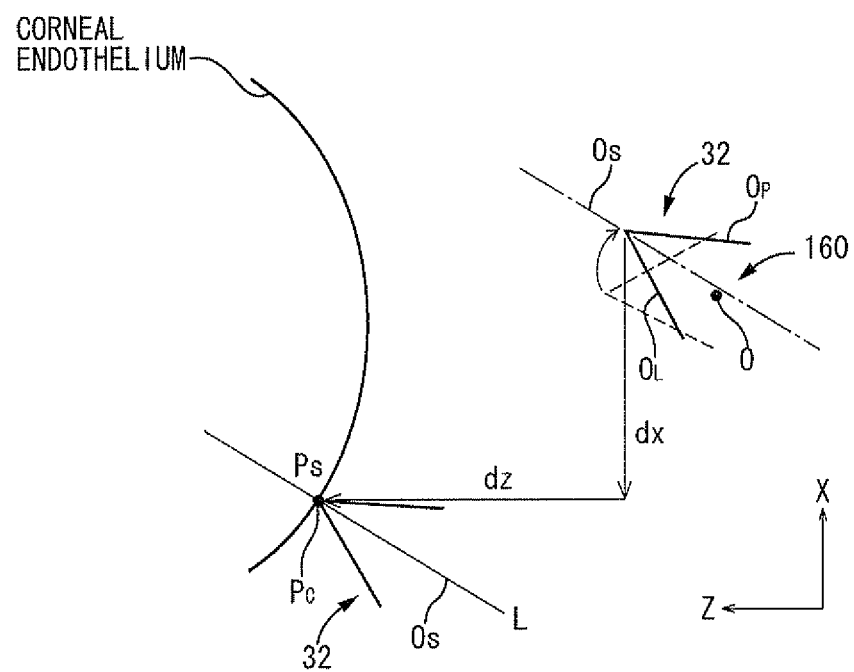
FIG. 17 is an illustrative drawing for explaining a mode different in an inclination angle changing means.
Figures 18A, 18B:
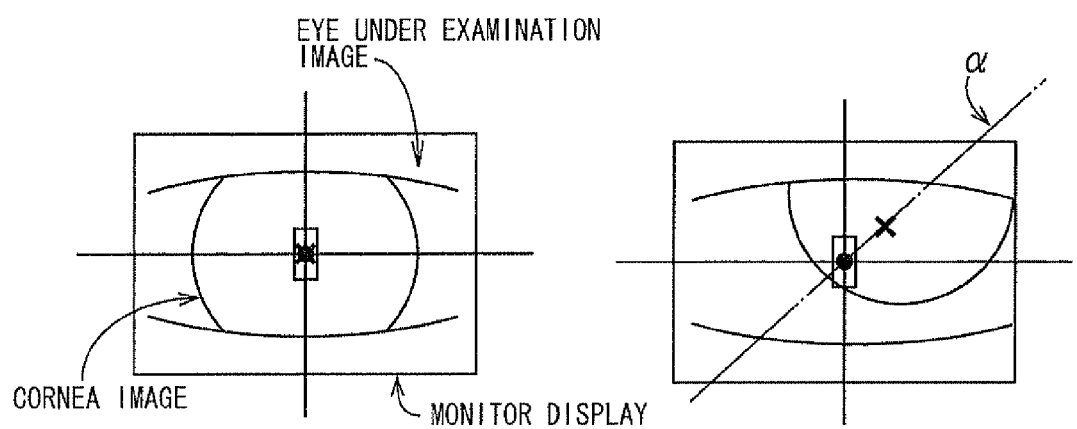
FIGS. 18A and 18B are illustrative drawings for explaining issues of the cornea imaging apparatus.

For example, the inclination angle changing means that changes the inclination angle of the imaging center axis of the imaging mechanism against the front-sight axis of the eye under examination E is not limited to the rack pinion mechanism using the rack 104 of the circular arc rails 102, 142 and 152 with the pinion 108 of the above embodiments. As schematically shown in FIG. 17, it is possible, for example, to materialize the specular optical system 32, as an imaging mechanism, by a rotation mechanism 160 that makes it rotatable around the vertical axis O (an axis extending perpendicular to the printed surface in FIG. 17) at a given position. In such structure, aligning the specular optical system 32 with the imaging point Ps on the corneal endothelium can be performed by means of rotating the specular optical system 32 around the vertical axis O using the rotation mechanism 160 and making the imaging center axis Os parallel to the normal vector L of the corneal endothelium at the imaging point Ps before setting the imaging center axis Os to the normal vector direction of the conical endothelium by actuating the X-axis actuating mechanism 90 and Z-axis actuating mechanism 94 to move them by dx and dz in the X and Z directions, respectively.

Also, in the above first embodiment, a mode of taking images consecutively at six locations on the corneal endothelium was exemplified, but the cornea imaging apparatus of the present invention can take an image at any single location on the corneal endothelium. In addition, taking consecutive images at multiple locations can be performed at least at two locations, and in case of wide-range endothelium images (shown as 134 in FIG. 12), a combination of at least two images of the endothelium (shown as 132 in FIG. 12) can be used. Furthermore, it is possible, as a matter of course, to limit the number of imaging locations by taking images consecutively at particular locations in the circumferential direction of the corneal endothelium, as described above, or the consecutive images can be taken by calculating the endothelial configuration of limited portions that need to be imaged. More specifically, the positions of preliminarily measured points Pt1 to Pt3 on the corneal endothelium shown in FIG. 9A can be set by specifying the portions to be imaged in the circumferential direction thereof, and by doing it, the preliminary curvature radius $r_t$ can be determined accurately within a limited area of imaging. Also, the consecutive imaging of the corneal endothelium can be limited within a particular area in the circumferential direction thereof by calculating the corneal endothelial configuration only for portions that need to be imaged by means of reducing the measurement points Pm1 to Pm5 shown in FIG. 9B, or specifying the positions of the measurement points Pm1 to Pm5 to be set up so as to limit the measured positions P1 to P5 of the corneal endothelium to the portions that need to be imaged. This can further reduce the time spent for completing the imaging. Also, in the above embodiment, images of the endothelium around the cornea were taken with the front-sight axis of the eye under examination E fixed straight ahead, but it can be done by providing a fixation target light source that retains the collimation axis of the eye under examination E at a position away from straight ahead and keeping the eye under examination E sideways.

Moreover, measurements of the corneal endothelium (see S5 of FIG. 6 and FIG. 9) do not necessarily have to be performed using a line sensor, but the position of the corneal endothelium can be determined, for example, from the displacement distance of the imaging apparatus from the time of detecting the corneal epithelium to detecting the corneal endothelium by measuring the amount of the light flux reflected from the eye under examination using a photo diode while the imaging apparatus is advanced, or as described in U.S. Pat. No. 7,572,010 and European Unexamined Patent Publication No. 1974657 of the patents previously applied for by this applicant, the corneal endothelium images can be taken consecutively at multiple locations as the imaging apparatus is displaced along the imaging center axis to determine the position of the corneal endothelium from the position of the imaging apparatus at the moment when a clear image of the endothelium is obtained.

Also, the instrumental optical system 12 of the above embodiment is just an example, and of course the configuration and arrangement locations and the like of the optical parts constituting each optical system such as lenses and slits are not limited to the configuration described above, and it is needless to say that the optical parts such as lenses, slits and collimator lenses and so forth can be provided properly as needed.

What is claimed is:

1. A cornea imaging apparatus comprising:
a collimation axis holding mechanism including a fixation target that keeps a collimation axis of an eye under examination at a given position;
an imaging mechanism containing an illumination optical system with an illumination light source that obliquely illuminates a slit light flux on the eye under examination and a cornea imaging optical system having a photoelectric element that takes images of a corneal endothelium by receiving the slit light flux reflected from a cornea of the eye under examination;
a Z-direction actuating means that moves the imaging mechanism in a Z direction which is a direction of getting closer to or away from the eye under examination;
an X-direction actuating means and a Y-direction actuating means that move the imaging mechanism in X and Y directions respectively that are perpendicular to the Z direction;
an inclination angle changing means that changes an inclination angle of an imaging center axis of the imaging mechanism against the collimation axis of the eye under examination under a state where a position of the collimation axis of the eye under examination fixed and retained by the fixation target;
an endothelial configuration computing means that determines a corneal endothelial configuration of the eye under examination; and
a normal vector computing means for the endothelium that determines a normal vector direction at a given imaging position of the corneal endothelial configuration determined by the endothelial configuration computing means,
wherein at the imaging position, the inclination angle set by the inclination angle changing means and positions in the Z and X directions set by the Z and X direction actuating means, respectively, are set adjusted so as to align the imaging center axis of the imaging mechanism with the normal vector direction determined by the normal vector computing means for the endothelium.

2. The cornea imaging apparatus according to claim 1, wherein the inclination angle changing means comprises an oscillation mechanism that displaces the imaging mechanism in oscillation in a circumferential direction of the eye under examination.

3. The cornea imaging apparatus according to claim 1, wherein the imaging position is set at multiple locations in a circumferential direction of the eye under examination, and at the multiple locations, the imaging center axis of the imaging mechanism is set adjusted in sequence to the normal vector direction determined by the normal vector computing means for the endothelium under the state where the position of the collimation axis is fixed and retained by the fixation target so as to take consecutive images.

4. The cornea imaging apparatus according to claim 1, wherein the corneal endothelial configuration of the eye under examination is obtained by determining an estimated curvature value of the corneal endothelium using measured values of the cornea according to the endothelial configuration computing means.

5. The cornea imaging apparatus according to claim 4, wherein the estimated curvature value of the corneal endothelium is determined by measured values of a thickness of the cornea at not less than three locations apart from each other in a circumferential direction of the eye under examination according to the endothelial configuration computing means.

6. The cornea imaging apparatus according to claim 4, wherein the estimated curvature value of the corneal endothelium is followed in the endothelial configuration computing means and measurements of endothelium positions are taken based on the flux reflected from the cornea at multiple measurement points on the corneal endothelium, and the corneal endothelial configuration is obtained based on the measurements taken at the multiple measurement points.

7. The cornea imaging apparatus according to claim 1, wherein the Z-direction actuating means and X-direction actuating means comprise an imaging direction actuating means that moves the imaging mechanism in a direction of the imaging center axis.

8. The cornea imaging apparatus according to claim 1, wherein a keratometer that measures a corneal front curvature of the eye under examination on a horizontal plane is configured to comprise the collimation axis holding mechanism and a kerato-ring light source that directs multiple spot lights into the eye under examination around an optical axis of the fixation target.

9. A cornea imaging method of imaging a cornea of an eye under examination, the method comprising:
using the cornea imaging apparatus including: a collimation axis holding mechanism including a fixation target that keeps a collimation axis of an eye under examination at a given position; an imaging mechanism containing an illumination optical system with an illumination light source that obliquely illuminates a slit light flux on the eye under examination and a cornea imaging optical system having a photoelectric element that takes images of a corneal endothelium by receiving the slit light flux reflected from a cornea of the eye under examination; a Z-direction actuating means that moves the imaging mechanism in a Z direction which is a direction of getting closer to or away from the eye under examination; an X-direction actuating means and a Y-direction actuating means that move the imaging mechanism in X and Y directions respectively that are perpendicular to the Z direction; an inclination angle changing means that changes an inclination angle of an imaging center axis of the imaging mechanism against the collimation axis of the eye under examination under a state where a position of the collimation axis of the eye under examination fixed and retained by the fixation target; an endothelial configuration computing means that determines a corneal endothelial configuration of the eye under examination; and a normal vector computing means for the endothelium that determines a normal vector direction at a given imaging position of the corneal endothelial configuration determined by the endothelial configuration computing means, wherein at the imaging position, the inclination angle set by the inclination angle changing means and positions in the Z and X directions set by the Z and X direction actuating means, respectively, are set adjusted so as to align the imaging center axis of the imaging mechanism with the normal vector direction determined by the normal vector computing means for the endothelium;

an endothelial configuration computing step that determines the corneal endothelial configuration of the eye under examination by the endothelial configuration computing means under a state where the position of the collimation axis of the eye under examination is fixed and retained by the fixation target;

a normal vector computing step of the endothelium that determines by the normal vector computing means for the endothelium the normal vector direction at a given imaging position of the corneal endothelial configuration; and a position adjusting step of the imaging mechanism that, at the imaging position, adjusts and sets the inclination angle by the inclination angle changing means and the position in the Z direction by the Z-direction actuating means and the position in the X direction by the X-direction actuating means so as to align the imaging center axis of the imaging mechanism with the normal vector direction determined by the normal vector computing means for the endothelium.

10. The cornea imaging method according to claim 9, further comprising a consecutive imaging step wherein the imaging position is set at multiple locations in a circumferential direction of the eye under examination and the imaging center axis of the imaging mechanism is set adjusted in sequence to the normal vector direction determined by the normal vector computing means for the endothelium to take consecutive images at the multiple locations under a state where the position of the collimation axis of the eye under examination is fixed and retained by the fixation target.

* * * * *